United States Patent
Karp et al.

(10) Patent No.: US 7,419,991 B2
(45) Date of Patent: *Sep. 2, 2008

(54) 3-[5-(2-FLUORO-PHENYL)-[1,2,4]OXADIAZOL-3-YL]-BENZOIC ACID, COMPOSITIONS, AND METHODS FOR THE USE THEREOF

(75) Inventors: Gary Mitchell Karp, Princeton Junction, NJ (US); Seongwoo Hwang, Edison, NJ (US); Guangming Chen, Bridgewater, NJ (US); Neil Gregory Almstead, Princeton, NJ (US); Young-Choon Moon, Belle Mead, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 138 days.

This patent is subject to a terminal disclaimer.

(21) Appl. No.: 11/370,130

(22) Filed: Mar. 6, 2006

(65) Prior Publication Data

US 2006/0148864 A1    Jul. 6, 2006

Related U.S. Application Data

(63) Continuation of application No. 11/241,700, filed on Sep. 29, 2005, which is a continuation of application No. 10/822,259, filed on Apr. 9, 2004, now Pat. No. 6,992,096.

(60) Provisional application No. 60/461,988, filed on Apr. 11, 2003.

(51) Int. Cl.
*A61K 31/4245* (2006.01)
*C07D 271/06* (2006.01)

(52) U.S. Cl. .................. 514/364; 548/125; 548/131; 514/361

(58) Field of Classification Search .......... 548/125, 548/131; 514/361, 364
See application file for complete search history.

(56) References Cited

U.S. PATENT DOCUMENTS

| | | | |
|---|---|---|---|
| 3,192,103 A | 6/1965 | Sousa et al. | |
| 3,325,446 A | 6/1967 | Chang et al. | |
| 4,016,170 A | 4/1977 | Nadelson | |
| 4,022,901 A | 5/1977 | Narayanan et al. | |
| 4,135,910 A | 1/1979 | Howe | |
| 4,166,732 A | 9/1979 | Howe | |
| 4,210,762 A | 7/1980 | Howe | |
| 4,268,299 A | 5/1981 | Howe | |
| 4,414,221 A | 11/1983 | Parsons et al. | |
| 5,484,944 A | 1/1996 | Albaugh et al. | |
| 5,972,050 A | 10/1999 | Wiesenfeldt et al. | |
| 6,034,106 A | 3/2000 | Biftu et al. | |
| 6,180,648 B1 | 1/2001 | Kozikowski et al. | |
| 6,472,422 B2 | 10/2002 | Kozikowski et al. | |
| 6,498,151 B2 | 12/2002 | Li et al. | |
| 6,620,828 B2 | 9/2003 | Chu et al. | |
| 6,660,753 B2 | 12/2003 | Van Wagenen et al. | |
| 6,759,538 B2 | 7/2004 | Singh et al. | |
| 6,878,734 B2 | 4/2005 | Kalindijian et al. | |
| 6,992,096 B2 * | 1/2006 | Karp et al. | 514/364 |
| 7,041,685 B2 | 5/2006 | Cai et al. | |
| 7,112,595 B2 | 9/2006 | Van Wagenen et al. | |
| 7,153,880 B2 | 12/2006 | Singh et al. | |
| 7,202,262 B2 | 4/2007 | Karp et al. | |
| 2002/0025976 A1 | 2/2002 | Chu et al. | |
| 2002/0055521 A1 | 5/2002 | Kozikowski et al. | |
| 2002/0147188 A1 | 10/2002 | Cummings | |
| 2005/0154012 A1 | 7/2005 | Cai et al. | |

FOREIGN PATENT DOCUMENTS

| | | |
|---|---|---|
| DE | 4320801 | 1/1995 |
| EP | 675122 A2 | 10/1995 |
| JP | 51-143669 | 12/1976 |
| JP | 2001-247569 | 9/2001 |
| JP | 2002-105073 | 4/2002 |
| WO | WO 95/11885 | 5/1995 |
| WO | WO 97/09335 | 3/1997 |
| WO | WO 97/44333 | 11/1997 |
| WO | WO 97/46556 | 12/1997 |
| WO | WO 98/00465 | 1/1998 |
| WO | WO 98/33927 | 8/1998 |
| WO | WO 98/45263 | 10/1998 |
| WO | WO 98/49190 | 11/1998 |
| WO | WO 99/54317 | 10/1999 |
| WO | WO 00-21959 | 4/2000 |
| WO | WO 00-25768 | 5/2000 |
| WO | WO 00-38687 | 7/2000 |
| WO | WO 00-58278 | 10/2000 |

(Continued)

OTHER PUBLICATIONS

Mueller, G., *Chem. Ber.*, 19:1497 (1886).

(Continued)

*Primary Examiner*—Golam M Shameem
(74) *Attorney, Agent, or Firm*—Jones Day

(57) ABSTRACT

Novel 1,2,4-oxadiazole benzoic acid compounds, methods of using and pharmaceutical compositions comprising an 1,2,4-oxadiazole benzoic acid derivative are disclosed. The methods include methods of treating or preventing a disease ameliorated by modulation of premature translation termination or nonsense-mediated mRNA decay, or ameliorating one or more symptoms associated therewith.

24 Claims, No Drawings

FOREIGN PATENT DOCUMENTS

| | | |
|---|---|---|
| WO | WO 00-58280 | 10/2000 |
| WO | WO 00-58304 | 10/2000 |
| WO | WO 00-69810 | 11/2000 |
| WO | WO 00-75120 | 12/2000 |
| WO | WO 01-66534 | 9/2001 |
| WO | WO 01-85723 | 11/2001 |
| WO | WO 01-90101 | 11/2001 |
| WO | WO 02-072621 | 9/2002 |
| WO | WO 02-085869 | 10/2002 |
| WO | WO 02/100826 | 12/2002 |
| WO | WO 03-002559 | 1/2003 |
| WO | WO 2004/014370 | 2/2004 |
| WO | WO 2004/014902 | 2/2004 |
| WO | WO 2004/072050 | 8/2004 |
| WO | WO 2004/110351 | 12/2004 |
| WO | WO 2005/060961 | 7/2005 |
| WO | WO 2005/077373 | 8/2005 |

OTHER PUBLICATIONS

U.S. Appl. No. 60/269,847, filed Feb. 21, 2001, Van Wagenen et al.

U.S. Appl. No. 60/149,464, filed Aug. 19, 1999, Van Wagenen et al.

U.S. Appl. No. 60/405,472, filed Aug. 23, 2002, Singh et al.

U.S. Appl. No. 60/350,107, filed Nov. 2, 2001, Singh et al.

Sokolenko et al., 1972, Voprosy Khimii I Khimicheskoi Tekhnolugii, No. 27:107-112 (with English language abstract).

Deegan et al., 1999, "Parallel Synthesis of 1,2,4-Oxadiazoles Using CDI Activation," Bioorg. & Med. Chem. Lett. 9:209-212.

Carvalho et al., 1997, "Excited-state acidity of bifunctional compounds," J. Chem. Soc., Faraday Trans. 93(18):3325-3329.

Bencharif et al., 1997, "Anodic behavior of aromatic oximes: an electrochemical deoximation reaction," Electrochimica Acta. 42(23-24):3509-3512.

Fetizon et al., 1974, "Oxidations Par Le Carbonate D'Argent—XII," Tetrahedron 31:165-170 (with English language abstract).

Haugwitz et al., 1985, "Antiparasitic Agents. 6. Synthesis and Anthelmintic Activites of Novel Isothiocyanatophenyl-1,2,4-oxadiazoles," J. Med. Chem. 28:1234-1241.

Yurugi et al., 1973, "Studies of the Synthesis of N-Heterocyclic Compounds. IV. Hypocholesterolemic 1,2,4-Oxadiazole Derivatives," Chem. Pharm. Bull. 21(9):1885-1893.

* cited by examiner

US 7,419,991 B2

3-[5-(2-FLUORO-PHENYL)-[1,2,4]OXADIA-ZOL-3-YL]-BENZOIC ACID, COMPOSITIONS, AND METHODS FOR THE USE THEREOF

This application is a continuation of U.S. application Ser. No. 11/241,700, filed Sep. 29, 2005, which is a continuation of U.S. application Ser. No. 10/822,259, filed Apr. 9, 2004, now U.S. Pat. No. 6,992,096, which claims the benefit of U.S. Provisional Application No. 60/461,988, filed Apr. 11, 2003, each application being incorporated by reference herein in its entirety.

1. FIELD OF INVENTION

The invention relates to 1,2,4-oxadiazole benzoic acid compounds, compositions comprising the compounds and methods for treating or preventing diseases associated with nonsense mutations of mRNA by administering these compounds or compositions.

2. BACKGROUND OF THE INVENTION

Gene expression in cells depends upon the sequential processes of transcription and translation. Together, these processes produce a protein from the nucleotide sequence of its corresponding gene.

Transcription involves the synthesis of mRNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises the three phases of initiation, elongation and termination. Translation is initiated by the formation of an initiation complex consisting of protein factors, mRNA, tRNA, cofactors and the ribosomal subunits that recognize signals on the mRNA that direct the translation machinery to begin translation on the mRNA.

Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed. The completed polypeptide chain is released, and the ribosome subunits are recycled for another round of translation.

Mutations of the DNA sequence in which the number of bases is altered are categorized as insertion or deletion mutations (frameshift mutations) and can result in major disruptions of the genome. Mutations of the DNA that change one base into another are labeled missense mutations and are subdivided into the classes of transitions (one purine to another purine, or one pyrimidine to another pyrimidine) and transversions (a purine to a pyrimidine, or a pyrimidine to a purine).

Insertions, deletions, transition and transversion mutations can all result in a nonsense mutation, or chain termination mutation, in which the base mutation or frameshift mutation changes an amino acid codon into one of the three stop codons. These premature stop codons can produce aberrant proteins in cells as a result of premature translation termination. A nonsense mutation in an essential gene can be lethal and can also result in a number of diseases, such as, cancers, lysosomal storage disorders, the muscular dystrophies, cystic fibrosis and hemophilia, to name a few.

In bacterial and eukaryotic strains with nonsense mutations, suppression of the nonsense mutation can arise as a result of a mutation in one of the tRNA molecules so that the mutant tRNA can recognize the nonsense codon, as a result of mutations in proteins that are involved in the translation process, as a result of mutations in the ribosome (either the ribosomal RNA or ribosomal proteins), or by the addition of compounds known to alter the translation process (for example, cycloheximide or the aminoglycoside antibiotics). The result is that an amino acid will be incorporated into the polypeptide chain at the site of the nonsense mutation, and translation will not prematurely terminate at the nonsense codon. The inserted amino acid will not necessarily be identical to the original amino acid of the wild-type protein; however, many amino acid substitutions do not have a gross effect on protein structure or function. Thus, a protein produced by the suppression of a nonsense mutation would be likely to possess activity close to that of the wild-type protein. This scenario provides an opportunity to treat diseases associated with nonsense mutations by avoiding premature termination of translation through suppression of the nonsense mutation.

The ability of aminoglycoside antibiotics to promote readthrough of eukaryotic stop codons has attracted interest in these drugs as potential therapeutic agents in human diseases caused by nonsense mutations. One disease for which such a therapeutic strategy may be viable is classical late infantile neuronal ceroid lipofuscinosis (LINCL), a fatal childhood neurodegenerative disease with currently no effective treatment. Premature stop codon mutations in the gene CLN2, encoding the lysosomal tripeptidyl-peptidase 1 (TPP-I), are associated with disease in approximately half of children diagnosed with LINCL. The ability of the aminoglycoside gentamicin to restore TPP-I activity in LINCL cell lines has been examined. In one patient-derived cell line that was compound heterozygous for a commonly seen nonsense mutation (Arg208Stop) and a different rare nonsense mutation, approximately 7% of normal levels of TPP-I were maximally restored with gentamicin treatment. These results suggest that pharmacological suppression of nonsense mutations by aminoglycosides or functionally similar pharmaceuticals may have therapeutic potential in LINCL (Sleat et. al., *Eur. J. Ped. Neurol.* 5:Suppl A 57-62 (2001)).

In cultured cells having premature stop codons in the Cystic Fibrosis Transmembrane Conductance Regulator (CFTR) gene, treatment with aminoglycosides led to the production of full length CFTR (Bedwell et. al., *Nat. Med.* 3:1280-1284 (1997); Howard et. al. *Nat. Med.* 2: 467-469 (1996)). In a mouse model for Duchenne muscular dystrophy, gentamicin sulfate was observed to suppress translational termination at a premature stop codon resulting in full length dystrophin (Barton-Davis et. al., *J. Clin. Invest.* 104:375-381 (1999)). A small increase in the amount of full length dystrophin provided protection against contraction-induced damage in the mdx mice. The amino acid inserted at the site of the nonsense codon was not determined in these studies.

Small molecule therapeutics or prophylactics that suppress premature translation termination by mediating the misreading of the nonsense codon would be useful for the treatment of a number of diseases. The discovery of small molecule drugs, particularly orally bioavailable drugs, may lead to the introduction of a broad spectrum of selective therapeutics which can be used against disease caused by nonsense mutations.

3. SUMMARY OF THE INVENTION

The invention encompasses novel compounds, novel pharmaceutical compositions and novel methods of treatment. The compounds, compositions, and methods are, in part, based upon the modulation of premature translation termination and/or nonsense-mediated mRNA decay that play a role in a variety of diseases. Such diseases can occur due to the decreased amount of active protein produced as a result of premature termination of translation. The compounds of the invention allow the translation of mRNA to continue past the nonsense mutation resulting in the production of full length protein. Thus the invention encompasses compounds, compositions, and methods for treating and preventing a variety of diseases, in particular genetic diseases.

This invention encompasses 1,2,4-oxadiazole benzoic acid compounds of formula I:

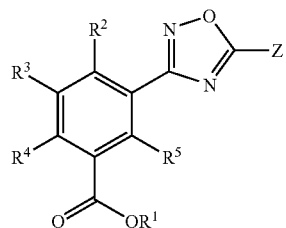

or pharmaceutically acceptable salts, hydrates, clathrates, prodrugs, polymorphs, stereoisomers, including enantiomers, diastereomers, racemates or mixtures of stereoisomers, thereof wherein:

Z is substituted or unsubstituted aryl, substituted or unsubstituted heteroaryl, substituted or unsubstituted cycloalkyl, substituted or unsubstituted alkyl, substituted or unsubstitued alkenyl, substituted or unsubstituted heterocycle, substituted or unsubstituted arylalkyl;

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —$(CH_2CH_2O)_nR^6$ or any biohydrolyzable group;

$R^2$, $R^3$, $R^4$, $R^5$ and $R^6$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, $CF_3$, $OCF_3$, $OCHF_2$, CN, COOH, $COOR^7$, $SO_2R^7$, $NO_2$, $NH_2$, or $N(R^7)_2$;

each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or $CF_3$; and n is an integer from 1 to 7.

In a related embodiment, the invention encompasses 1,2,4-oxadiazole benzoic acid compounds of the formula II:

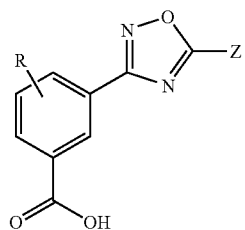

or pharmaceutically acceptable salts, hydrates, clathrates, or stereoisomers thereof wherein Z is defined as in formula I and R is hydrogen or halogen.

In a preferred embodiment of the invention, the compounds of formulas I and II are pharmaceutically acceptable salts, hydrates, clathrates, prodrugs, polymorphs, bio-hydrolyzable esters, racemates, or purified stereoisomers including, but not limited to, optically pure enantiomers and diastereomers.

The invention further encompasses methods of treating or preventing a disease ameliorated by modulation of premature translation termination or nonsense-mediated mRNA decay, or ameliorating one or more symptoms associated therewith comprising administering to a patient in need thereof a therapeutically or prophylactically effective amount of a compound of the formula I or II and pharmaceutically acceptable salts, hydrates, solvates, clathrates, prodrugs or polymorphs thereof. In a preferred embodiment, the disease is a genetic disease; a CNS disease; an inflammatory disease; a neurodegenerative disease; an autoimmune disease; a proliferative disease, in particular cancer; a cardiovascular disease; or a pulmonary disease; more preferably the disease includes, but is not limited to, amyloidosis, LINCL, hemophilia, Alzheimer's disease, atherosclerosis, giantism, dwarfism, hypothyroidism, hyperthyroidism, cystic fibrosis, aging, obesity, Parkinson's disease, Niemann Pick's disease, cystic fibrosis, familial hypercholesterolemia, retinitis pigmentosa, Duchenne muscular dystrophy, or Marfan syndrome.

The invention further encompasses methods of treating or preventing, or ameliorating a genetic disease one or more symptoms associated with or manifestations of a genetic disease comprising administering to a patient in need thereof a therapeutically or prophylactically effective amount of a compound of the formula I or II and pharmaceutically acceptable salts, hydrates, solvates, clathrates, prodrugs or polymorphs thereof. In a preferred embodiment, the disease is a CNS disease; an inflammatory disease; a neurodegenerative disease; a cardiovascular disease; an autoimmune disease; cancer; more preferably, the genetic disease includes, but is not limited to, amyloidosis, LINCL, hemophilia, Alzheimer's disease, atherosclerosis, giantism, dwarfism, hypothyroidism, hyperthyroidism, cystic fibrosis, aging, obesity, Parkinson's disease, Niemann Pick's disease, cystic fibrosis, familial hypercholesterolemia, retinitis pigmentosa, Duchenne muscular dystrophy, or Marfan syndrome.

The invention further relates to methods of treating, preventing, or ameliorating cancer or one or more symptoms associated with or manifestations of cancer comprising administering to a patient in need thereof a therapeutically or prophylactically effective amount of a compound of the formula I or II and pharmaceutically acceptable salts, hydrates, solvates, clathrates, prodrugs or polymorphs thereof.

In a preferred embodiment of the invention, the patient is a mammal, more preferably a human susceptible to or at risk of acquiring a genetic disease. In an alternative embodiment, the patient has undergone a screening process to determine the presence of a nonsense mutation comprising the steps of screening a subject or cells extracted therefrom by an acceptable nonsense mutation screening assay. In a related embodiment, the therapy is personalized in that the patient is screened for a nonsense mutation screening assay and treated by the administration of one or more compounds of the invention; particularly, the patient may be treated with a compound particularly suited for the mutations in question, e.g., depending upon the disease type, cell type, and the gene in question. In a further embodiment, the patient is an infant or child. In yet another embodiment, the invention encompasses the treatment of pregnant woman or the fetus directly.

In a still preferred embodiment of the invention, the compound is administered parenterally, transdermally, mucosally, nasally, buccally, sublingually, or orally; more preferably the compound is administered orally, most preferably the compound is administered orally in the form of a tablet, capsule or liquid.

The invention encompasses methods for modulating premature translation termination and/or nonsense-mediated mRNA decay. The invention further encompasses a method for suppressing premature translation termination and/or nonsense-mediated mRNA decay in a cell comprising contacting a cell exhibiting premature translation termination and/or nonsense-mediated mRNA decay with an effective amount of a compound of formula I or II. The invention further encompasses a method for inducing nonsense suppression in a cell comprising contacting a cell exhibiting a nonsense mutation with an effective amount of a compound of formula I or II. A nonsense codon can be present in the DNA or RNA of any type of cell and can arise naturally or result from mutagenesis. Accordingly, cells encompassed by the present methods include animal cells, mammalian cells, bacterial cells, plant cells and virally infected cells. In one embodiment, the nonsense codon was present in the progenitor DNA. In another embodiment, the nonsense codon resulted from mutagenesis.

Without being limited to any particular theory, the ability of the compounds of formula I or II to promote readthrough of stop codons makes them useful in the treatment or prevention of any disease which is caused in whole or in part by a nonsense mutation. Such diseases can occur due to the decreased amount of active protein produced as a result of premature termination of translation. Without being limited to any particular theory, the compounds of formula I or II allow the translation of mRNA to continue past the nonsense mutation resulting in the production of full length protein. A powerful aspect of the invention is that the therapeutic activity of compounds of formula I or II are not necessarily disease specific, instead are effective at treating of preventing any disease associated with a nonsense mutation. Further, the methods of the invention may be patient specific. That is, a patient may be screened to determine if this disease is associated with a nonsense mutation. If so, they can be treated with a compound of the invention.

The compounds of formula I or II are useful for treating or preventing genetic diseases. Genetic diseases that can be treated or prevented by compounds of formula I or II include cancer, autoimmune disease, blood disease, collagen disease, diabetes, inflammatory diseases or a central nervous system disease.

3.1 DEFINITIONS

As used herein, "premature translation termination" refers to the result of a mutation that changes a codon corresponding to an amino acid to a stop codon.

As used herein, "nonsense-mediated mRNA decay" refers to any mechanism that mediates the decay of mRNAs containing a premature translation termination codon.

As used herein, a "premature termination codon" or "premature stop codon" refers to the occurrence of a stop codon where a codon corresponding to an amino acid should be.

As used herein, a "nonsense mutation" is a point mutation changing a codon corresponding to an amino acid to a stop codon.

As used herein, "nonsense suppression" refers to the inhibition or suppression of premature translation and/or nonsense-mediated mRNA decay.

As used herein, "modulation of premature translation termination and/or nonsense-mediated mRNA decay" refers to the regulation of gene expression by altering the level of nonsense suppression. For example, if it is desirable to increase production of a defective protein encoded by a gene with a premature stop codon, i.e., to permit readthrough of the premature stop codon of the disease gene so translation of the gene can occur, then modulation of premature translation termination and/or nonsense-mediated mRNA decay entails up-regulation of nonsense suppression. Conversely, if it is desirable to promote the degradation of an mRNA with a premature stop codon, then modulation of premature translation termination and/or nonsense-mediated mRNA decay entails down-regulation of nonsense suppression.

As used herein, the term "patient" means an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human. In certain embodiments, the patient is an infant, child, adolescent or adult. In one embodiment, it has been determined through pre-screening that the patient possesses a non-sense mutation. In another embodiment, it has been determined through pre-screening which non-sense mutation the patient has (i.e., UAA, UGA, or UAG). In another embodiment, the patient is infected with bacterial cells (e.g., *Pseudomonas aeruginosa*). In another embodiment, the cells of the patient are virally infected.

As used herein, unless otherwise specified, the term "substituted" means a group substituted by one to four or more substituents, such as, halo, trifluoromethyl, trifluoromethoxy, hydroxy, alkoxy, cycloalkyoxy, heterocylooxy, oxo, alkanoyl, alkylcarbonyl, cycloalkyl, aryl, aryloxy, aralkyl alkanoyloxy, cyano, azido, amino, alkylamino, arylamino, aralkylamino, cycloalkylamino, heterocycloamino, mono and disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, carboxy, carbamyl (e.g. $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclo, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. In a particular embodiment, the term substituted does not mean cyano.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, unless otherwise specified the term "alkenyl group" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, unless otherwise specified the term "alkynyl group" means a straight chain or branched non-cyclic hydrocarbon having from 2 to 20 carbon atoms, more preferably 2-10 carbon atoms, most preferably 2-6 carbon atoms, and including at lease one carbon-carbon triple bond. Representative straight chain and branched -($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, unless otherwise specified the term "halogen" or "halo" means fluorine, chlorine, bromine, or iodine.

As used herein, unless otherwise specified the term "alkyl sulfonyl" means -Alkyl-$SO_3H$ or —$SO_3$-alkyl, wherein alkyl is defined as above, including —$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$, and the like.

As used herein, unless otherwise specified the term "carboxyl" and "carboxy" mean —COOH.

As used herein, unless otherwise specified the term "alkoxy" means —O-(alkyl), wherein alkyl is defined above, including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like.

As used herein, unless otherwise specified the term "alkoxycarbonyl" means —C(=O)O-(alkyl), wherein alkyl is defined as above, including —C(=O)O—$CH_3$, —C(=O)O—$CH_2CH_3$, —C(=O)O—$(CH_2)_2CH_3$, —C(=O)O—$(CH_2)_3CH_3$, —C(=O)O—$(CH_2)_4CH_3$, —C(=O)O—$(CH_2)_5CH_3$, and the like. In a preferred embodiment, the esters are biohydrolyzable (i.e., the ester is hydrolyzed to a carboxylic acid in vitro or in vivo).

As used herein, unless otherwise specified the term "alkoxyalkyl" means -(alkyl)-O-(alkyl), wherein each "alkyl" is independently an alkyl group as defined above, including —$CH_2OCH_3$, —$CH_2OCH_2CH_3$, —$(CH_2)_2OCH_2CH_3$, —$(CH_2)_2O(CH_2)_2CH_3$, and the like.

As used herein, unless otherwise specified the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. A carbocyclic aryl group can be unsubstituted or substituted.

As used herein, unless otherwise specified the term "heteroaryl" means a carbocyclic aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or tricyclic compounds as well as fused heterocycle moieties. Representative heteroaryls are triazolyl, tetrazolyl, oxadiazolyl, pyridyl, furyl, benzofuranyl, thiophenyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl and oxazolyl. A group can be unsubstituted or substituted.

As used herein, unless otherwise specified the term "aryloxy" means —O-aryl group, wherein aryl is as defined above. An aryloxy group can be unsubstituted or substituted.

As used herein, unless otherwise specified the term "arylalkyl" means -(alkyl)-(aryl), wherein alkyl and aryl are defined above, including, but not limited to —$(CH_2)$phenyl, —$(CH_2)_2$phenyl, —$(CH_2)_3$phenyl, —CH(phenyl)$_2$, —CH(phenyl)$_3$, —$(CH_2)$tolyl, —$(CH_2)$anthracenyl, —$(CH_2)$fluorenyl, —$(CH_2)$indenyl, —$(CH_2)$azulenyl, —$(CH_2)$naphthyl, and the like.

As used herein, unless otherwise specified the term "heteroarylalkyl" means -(alkyl)-(heteroaryl), wherein alkyl and heteroaryl are defined above, including, but not limited to —$(CH_2)$pyridyl, —$(CH_2)_2$pyridyl, —$(CH_2)_3$pyridyl, —CH(pyridyl)$_2$, —C(pyridyl)$_3$, —$(CH_2)$triazolyl, —$(CH_2)$tetrazolyl, —$(CH_2)$oxadiazolyl, —$(CH_2)$furyl, —$(CH_2)$benzofuranyl, —$(CH_2)$thiophenyl, —$(CH_2)$benzothiophenyl, and the like.

As used herein, unless otherwise specified the term "arylalkyloxy" means —O-(alkyl)-(aryl), wherein alkyl and aryl are defined above, including, but not limited to —O—$(CH_2)_2$phenyl, —O—$(CH_2)_3$phenyl, —O—CH(phenyl)$_2$, —O—CH(phenyl)$_3$, —O—$(CH_2)$tolyl, —O—$(CH_2)$anthracenyl, —O—$(CH_2)$fluorenyl, —O—$(CH_2)$indenyl, —O—$(CH_2)$azulenyl, —O—$(CH_2)$naphthyl, and the like.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted. Examples of cycloalkyl groups include, but are not limited to, ($C_3$—$C_7$)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, unless otherwise specified the term "heterocyclyl" means a monocyclic or polycyclic ring comprising carbon and hydrogen atoms, optionally having 1 to 4 multiple bonds, and the ring atoms contain at least one heteroatom, preferably 1 to 3 heteroatoms, independently selected from nitrogen, oxygen, and sulfur. Heterocyclyl ring structures include compounds having one or more ring structures such as mono-, bi-, or tricylic compounds. Preferably, the heterocyclyl group is a monocyclic ring or bicyclic ring. Representative heterocycles include, but are not limited to morpholinyl, pyrrolidinonyl, pyrrolidinyl, piperidinyl, hydantoinyl, valerolactanyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like. A heterocyclyl ring can be unsubstituted or substituted.

As used herein, unless otherwise specified the term "cycloalkyloxy" means —O-(cycloalkyl), wherein cycloalkyl is defined above.

As used herein, unless otherwise specified the term "cycloalkylalkyloxy" means —O-(alkyl)-(cycloalkyl), wherein cycloalkyl and alkyl are defined above, including, but not limited to —O-cyclopropyl, —O-cyclobutyl, —O-cyclopentyl, —O-cyclohexyl, —O-cycloheptyl and the like.

As used herein, unless otherwise specified the term "aminoalkoxy" means —O-(alkyl)-$NH_2$, wherein alkyl is defined above, including, but not limited to —O—$CH_2$—$NH_2$, —O—$(CH_2)_2$—$NH_2$, —O—$(CH_2)_3$—$NH_2$, —O—$(CH_2)_4$—$NH_2$, —O—$(CH_2)_5$—$NH_2$, and the like.

As used herein, unless otherwise specified the term "alkylamino" means —NH(alkyl) or —N(alkyl)(alkyl), wherein alkyl is defined above, including, but not limited to $NHCH_3$, —$NHCH_2CH_3$, —$NH(CH_2)_2CH_3$, —$NH(CH_2)_3CH_3$, —$NH(CH_2)_4CH_3$, —$NH(CH_2)_5CH_3$, —$N(CH_3)_2$, —$N(CH_2CH_3)_2$, —$N((CH_2)_2CH_3)_2$, —$N(CH_3)(CH_2CH_3)$, and the like.

As used herein, unless otherwise specified the term "arylamino" means —NH(aryl), wherein aryl is defined above, including, but not limited to —NH(phenyl), —NH(tolyl), —NH(anthracenyl), —NH(fluorenyl), —NH(indenyl), —NH(azulenyl), —NH(pyridinyl), —NH(naphthyl), and the like.

As used herein, unless otherwise specified the term "arylalkylamino" means —NH-(alkyl)-(aryl), wherein alkyl and aryl are defined above, including —NH—$CH_2$-(phenyl), —NH—$CH_2$-(tolyl), —NH—$CH_2$-(anthracenyl), —NH—$CH_2$-(fluorenyl), —NH—$CH_2$-(indenyl), —NH—$CH_2$-(azulenyl), —NH—$CH_2$-(pyridinyl), —NH—$CH_2$-(naphthyl), —NH—$(CH_2)_2$-(phenyl) and the like.

As used herein, unless otherwise specified the term "cycloalkylamino" means —NH-(cycloalkyl), wherein cycloalkyl is defined above, including —NH-cyclopropyl, —NH-cyclobutyl, —NH-cyclopentyl, —NH-cyclohexyl, —NH-cycloheptyl, and the like.

As used herein, unless otherwise specified the term "aminoalkyl" means -(alkyl)-$NH_2$, wherein alkyl is defined above, including —$CH_2$—$NH_2$, —$(CH_2)_2$—$NH_2$, —$(CH_2)_3$—$NH_2$, —$(CH_2)_4$—$NH_2$, —$(CH_2)_5$—$NH_2$ and the like.

As used herein, unless otherwise specified the term "alkylaminoalkyl" means -(alkyl)-NH(alkyl) or -(alkyl)-N(alkyl)(alkyl), wherein each "alkyl" is independently an alkyl group defined above, including —$CH_2$—NH—$CH_3$, —$CH_2$—$NHCH_2CH_3$, —$CH_2$—$NH(CH_2)_2CH_3$, —$CH_2$—$NH(CH_2)_3CH_3$, —$CH_2$—$NH(CH_2)_4CH_3$, —$CH_2$—$NH(CH_2)_5CH_3$, —$(CH_2)_2$—NH—$CH_3$, —$CH_2$—$N(CH_3)_2$, —$CH_2$—N$(CH_2CH_3)_2$, —$CH_2$—$N((CH_2)_2CH_3)_2$, —$CH_2$—$N(CH_3)(CH_2CH_3)$, —$(CH_2)_2$—$N(CH_3)_2$, and the like.

As used herein, a "therapeutically effective amount" refers to that amount of the compound of the invention or other active ingredient sufficient to provide a therapeutic benefit in the treatment or management of the disease or to delay or minimize symptoms associated with the disease. Further, a therapeutically effective amount with respect to a compound of the invention means that amount of therapeutic agent alone, or in combination with other therapies, that provides a therapeutic benefit in the treatment or management of the disease. Used in connection with an amount of a compound of the invention, the term can encompass an amount that improves overall therapy, reduces or avoids symptoms or causes of disease, or enhances the therapeutic efficacy of or synergies with another therapeutic agent.

As used herein, a "prophylactically effective amount" refers to that amount of a compound of the invention or other active ingredient sufficient to result in the prevention, recurrence or spread of the disease. A prophylactically effective amount may refer to the amount sufficient to prevent initial disease or the recurrence or spread of the disease or the occurrence of the disease in a patient, including but not limited to those predisposed to the disease. A prophylactically effective amount may also refer to the amount that provides a prophylactic benefit in the prevention of the disease. Further, a prophylactically effective amount with respect to a compound of the invention means that amount alone, or in combination with other agents, that provides a prophylactic benefit in the prevention of the disease. Used in connection with an amount of a compound of the invention, the term can encompass an amount that improves overall prophylaxis or enhances the prophylactic efficacy of or synergies with another prophylactic agent.

As used herein, a "therapeutic protocol" refers to a regimen of timing and dosing of one or more therapeutic agents.

As used herein, a "prophylactic protocol" refers to a regimen of timing and dosing of one or more prophylactic agents.

A used herein, a "protocol" includes dosing schedules and dosing regimens.

As used herein, "in combination" refers to the use of more than one prophylactic and/or therapeutic agents.

As used herein, the terms "manage", "managing" and "management" refer to the beneficial effects that a subject derives from a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the onset recurrence, spread or of the disease in a subject resulting from the administration of a prophylactic or therapeutic agent.

As used herein, the terms "treat", "treating" and "treatment" refer to the eradication or amelioration of the disease or symptoms associated with the disease. In certain embodiments, such terms refer to minimizing the spread or worsening of the disease resulting from the administration of one or more prophylactic or therapeutic agents to a subject with such a disease.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Other examples of salts are well known in the art, see, e.g., *Remington's Pharmaceutical Sciences*, 18th ed., Mack Publishing, Easton Pa. (1990).

As used herein and unless otherwise indicated, the term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocycle and heteroaromatic amines, and polyether amines.

As used herein and unless otherwise indicated, the term "optically pure" or "stereomerically pure" means a the stereoisomer of a compound is substantially free of the other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4. DETAILED DESCRIPTION OF THE INVENTION 4.1 Compounds of the Invention

This invention encompasses 1,2,4-oxadiazole benzoic acid compounds of formla I:

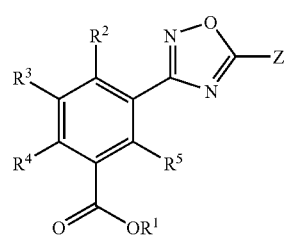

or pharmaceutically acceptable salts, hydrates, clathrates, prodrugs, polymorphs, stereoisomers, including enantiomers, diastereomers, racemates or mixtures of stereoisomers, thereof wherein:

Z is substituted or unsubstituted aryl, substituted or unsubstituted heteroaryl, substituted or unsubstituted cycloalkyl, substituted or unsubstitued alkyl, substituted or unsubstitued alkenyl, substituted or unsubstituted heterocycle, substituted or unsubstituted arylalkyl;

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —$(CH_2CH_2O)_nR^6$ or any biohydrolyzable group;

$R^2$, $R_3$, $R^4$, $R^5$ and $R^6$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, $CF_3$, $OCF_3$, $OCHF_2$, CN, COOH, $COOR^7$, $SO_2R^7$, $NO_2$, $NH_2$, or $N(R^7)_2$;

each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or $CF_3$; and n is an integer from 1 to 7.

In an alternative embodiment, the invention encompasses a compound of Formula I wherein when $R^1$, $R^2$, $R^3$, $R^4$, and $R^5$ are hydrogen, Z is not methyl, 2-carboxy ethyl, 3-(4-pyridinyl)propyl, or 2-(4-piperidinyl) ethyl.

In a preferred embodiment, the invention encompasses a compound of Formula I wherein $R^1$ is H.

In a preferred embodiment, the invention encompasses a compound of Formula I wherein $R^1$ is any biohydrolyzable group other than H.

In a related embodiment, the invention encompasses 1,2,4-oxadiazole benzoic acid compounds of the formula II:

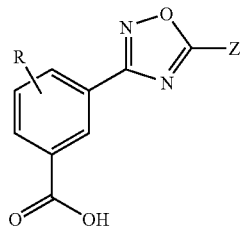

or pharmaceutically acceptable salts, hydrates, clathrates, or stereoisomers thereof Z is substituted or unsubstituted aryl, substituted or unsubstituted heteroaryl, substituted or unsubstituted cycloalkyl, substituted or unsubstituted alkyl, substituted or unsubstitued alkenyl, substituted or unsubstituted heterocycle, substituted or unsubstituted arylalkyl; and R is hydrogen or halogen.

In one embodiment R is the halogen, fluorine. In a preferred embodiment, R is hydrogen.

In a preferred embodiment, the invention encompasses a compound of Formula I or II wherein Z is p-Tolyl; (4-Chloromethyl-phenyl); (2-Chloro-pyridin-3-yl); (2-Fluoro-phenyl); (3,4-Difluoro-phenyl); (4-Methoxy-phenyl); Benzo[1,3]dioxol-yl; (4-Ethyl-phenyl); o-Tolyl; (2-Chloro-phenyl); (3-Methyl-thiophen-2-yl); Benzo[b]thiophen-2-yl; (3-Fluoro-phenyl); (4-tert-Butyl-phenyl); (2-Methoxy-phenyl); (2,6-Difluoro-phenyl); Thiophen-2-yl; (2,4-Difluoro-phenyl); (3-Chloro-phenyl); m-Tolyl; (4-Trifluoromethyl-phenyl); (4-Fluoro-phenyl); (3-Methoxy-phenyl); Phenyl; (2,6-Difluoro-phenyl); (2,5-Dimethyl-furan-3-yl); (4-Pyrrol-1-yl-phenyl); (3-Dimethylamino-phenyl); Biphenyl-4-yl; (4-Dimethylamino-phenyl); Benzo[1,2,5]oxadiazol-yl; m-Tolyl; (2-Trifluoromethyl-phenyl); (6-Chloro-pyridin-3-yl); (3,Bis-trifluoromethyl-phenyl); Furan-2-yl; (4-Nitro-phenyl); (3,4-Dimethoxy-phenyl); (3-Trifluoromethoxy-phenyl); Naphthalen-1-yl; Cyclohexyl; Pyridin-3-yl; Pyridin-4-yl; Cyclopentyl; Cyclopropyl; (4-Pentyloxy-phenyl); (3,4,5-Trimethoxy-phenyl); (4-Isobutyl-phenyl); Cyclobutyl; 5-(1-Acetyl-piperidin-4-yl); 5-Isoxazol-5-yl; [3-(2-Chloro-6-fluoro-phenyl)-5-methyl-isoxazol-4-yl] or [3-(2-Chloro-phenyl)-5-methyl-isoxazol-4-yl]; more preferably Z is (3-Fluoro-phenyl), more preferably Z is (4-Fluoro-phenyl), even more preferably Z is (2-Fluoro-phenyl).

In a specific embodiment, the invention encompasses a compound of Formula I or II wherein Z is not 4-cyano-phenyl.

Preferred compounds of the invention include, but are not limited to,
3-(5-p-Tolyl-[1,2,4]oxadiazol-3-yl)-benzoic acid;
3-[5-(4-Chloromethyl-phenyl)-[1,2,4]oxadiazol-3-yl]-benzoic acid;
3-[5-(2-Chloro-pyridin-3-yl)-[1,2,4]oxadiazol-3-yl]-benzoic acid;
3-[5-(2-Fluoro-phenyl)-[1,2,4]oxadiazol-3-yl]-benzoic acid;
3-[5-(3,4-Difluoro-phenyl)-[1,2,4]oxadiazol-3-yl]-benzoic acid;
3-[5-(4-Methoxy-phenyl)-[1,2,4]oxadiazol-3-yl]-benzoic acid;
3-(5-Benzo[1,3]dioxol-5-yl-[1,2,4]oxadiazol-3-yl)-benzoic acid;
3-[5-(4-Ethyl-phenyl)-[1,2,4]oxadiazol-3-yl]-benzoic acid;
3-(5-o-Tolyl-[1,2,4]oxadiazol-3-yl)-benzoic acid;
3-[5-(2-Chloro-phenyl)-[1,2,4]oxadiazol-3-yl]-benzoic acid;
3-[5-(3-Methyl-thiophen-2-yl)-[1,2,4]oxadiazol-3-yl]-benzoic acid;
3-(5-Benzo[b]thiophen-2-yl-[1,2,4]oxadiazol-3-yl)-benzoic acid;
3-[5-(3-Fluoro-phenyl)-[1,2,4]oxadiazol-3-yl]-benzoic acid;
3-[5-(4-tert-Butyl-phenyl)-[1,2,4]oxadiazol-3-yl]-benzoic acid;
3-[5-(2-Methoxy-phenyl)-[1,2,4]oxadiazol-3-yl]-benzoic acid;
3-[5-(2,5-Difluoro-phenyl)-[1,2,4]oxadiazol-3-yl]-benzoic acid;
3-(5-Thiophen-2-yl-[1,2,4]oxadiazol-3-yl)-benzoic acid;
3-[5-(2,4-Difluoro-phenyl)-[1,2,4]oxadiazol-3-yl]-benzoic acid;
3-[5-(3-Chloro-phenyl)-[1,2,4]oxadiazol-3-yl]-benzoic acid;
3-(5-m-Tolyl-[1,2,4]oxadiazol-3-yl)-benzoic acid;
3-[5-(4-Trifluoromethyl-phenyl)-[1,2,4]oxadiazol-3-yl]-benzoic acid;
3-[5-(4-Fluoro-phenyl)-[1,2,4]oxadiazol-3-yl]-benzoic acid;

3-[5-(3-Methoxy-phenyl)-[1,2,4]oxadiazol-3-yl]-benzoic acid;
3-(5-Phenyl-[1,2,4]oxadiazol-3-yl)-benzoic acid;
3-[5-(2,6-Difluoro-phenyl)-[1,2,4]oxadiazol-3-yl]-benzoic acid;
3-[5-(2,5-Dimethyl-furan-3-yl)-[1,2,4]oxadiazol-3-yl]-benzoic acid;
3-[5-(4-Pyrrol-1-yl-phenyl)-[1,2,4]oxadiazol-3-yl]-benzoic acid;
3-[5-(3-Dimethylamino-phenyl)-[1,2,4]oxadiazol-3-yl]-benzoic acid;
3-(5-Biphenyl-4-yl-[1,2,4]oxadiazol-3-yl)-benzoic acid;
3-[5-(4-Dimethylamino-phenyl)-[1,2,4]oxadiazol-3-yl]-benzoic acid;
3-(5-Benzo[1,2,5]oxadiazol-5-yl-[1,2,4]oxadiazol-3-yl)-benzoic acid;
3-(5-m-Tolyl-[1,2,4]oxadiazol-3-yl)-benzoic acid;
3-[5-(2-Trifluoromethyl-phenyl)-[1,2,4]oxadiazol-3-yl]-benzoic acid;
3-[5-(6-Chloro-pyridin-3-yl)-[1,2,4]oxadiazol-3-yl]-benzoic acid;
3-[5-(3,5-Bis-trifluoromethyl-phenyl)-[1,2,4]oxadiazol-3-yl]-benzoic acid;
3-(5-Furan-2-yl-[1,2,4]oxadiazol-3-yl)-benzoic acid;
3-[5-(4-Nitro-phenyl)-[1,2,4]oxadiazol-3-yl]-benzoic acid;
3-[5-(3,4-Dimethoxy-phenyl)-[1,2,4]oxadiazol-3-yl]-benzoic acid;
3-[5-(3-Trifluoromethoxy-phenyl)-[1,2,4]oxadiazol-3-yl]-benzoic acid;
3-(5-Naphthalen-1-yl-[1,2,4]oxadiazol-3-yl)-benzoic acid;
3-(5-Cyclohexyl-[1,2,4]oxadiazol-3-yl)-benzoic acid;
3-(5-Pyridin-3-yl-[1,2,4]oxadiazol-3-yl)-benzoic acid;
3-(5-Pyridin-4-yl-[1,2,4]oxadiazol-3-yl)-benzoic acid;
3-(5-Cyclopentyl-[1,2,4]oxadiazol-3-yl)-benzoic acid;
3-(5-Cyclopropyl-[1,2,4]oxadiazol-3-yl)-benzoic acid;
3-[5-(4-Pentyloxy-phenyl)-[1,2,4]oxadiazol-3-yl]-benzoic acid;
3-[5-(3,4,5-Trimethoxy-phenyl)-[1,2,4]oxadiazol-3-yl]-benzoic acid;
3-[5-(4-Isobutyl-phenyl)-[1,2,4]oxadiazol-3-yl]-benzoic acid;
3-(5-Cyclobutyl-[1,2,4]oxadiazol-3-yl)-benzoic acid;
3-[5-(1-Acetyl-piperidin-4-yl)-[1,2,4]oxadiazol-3-yl]-benzoic acid;
3-(5-Isoxazol-5-yl-[1,2,4]oxadiazol-3-yl)-benzoic acid;
3-{5-[3-(2-Chloro-6-fluoro-phenyl)-5-methyl-isoxazol-4-yl]-[1,2,4]oxadiazol-3-yl}-benzoic acid;
3-(5-Isopropyl-[1,2,4]oxadiazol-3-yl)-benzoic acid;
3-(5-tert-Butyl-[1,2,4]oxadiazol-3-yl)-benzoic acid; 3-(5-Butyl-[1,2,4]oxadiazol-3-yl)-benzoic acid;
3-(5-Propenyl-[1,2,4]oxadiazol-3-yl)-benzoic acid;
3-[5-(4-Chloro-benzyl)-[1,2,4]oxadiazol-3-yl]-benzoic acid;
3-[5-(4-Chloro-phenoxymethyl)-[1,2,4]oxadiazol-3-yl]-benzoic acid;
3-(5-Benzyl-[1,2,4]oxadiazol-3-yl)-benzoic acid;
3-(5-Methoxymethyl-[1,2,4]oxadiazol-3-yl)-benzoic acid;
3-[5-(1-Phenyl-propyl)-[1,2,4]oxadiazol-3-yl]-benzoic acid;
3-[5-(4-Fluoro-benzyl)-[1,2,4]oxadiazol-3-yl]-benzoic acid;
3-[5-(3-Chloro-phenoxymethyl)-[1,2,4]oxadiazol-3-yl]-benzoic acid;
3-[5-(6-Chloro-pyridin-3-yl)-[1,2,4]oxadiazol-3-yl]-benzoic acid;
3-(5-Cyclopentylmethyl-[1,2,4]oxadiazol-3-yl)-benzoic acid;
3-[5-(4-Methoxy-benzyl)-[1,2,4]oxadiazol-3-yl]-benzoic acid;
3-[5-(2,3-Difluoro-phenyl)-[1,2,4]oxadiazol-3-yl]-benzoic acid;
3-[5-(2-Fluoro-5-methyl-phenyl)-[1,2,4]oxadiazol-3-yl]-benzoic acid;
3-[5-(2-Methylsulfanyl-pyridin-3-yl)-[1,2,4]oxadiazol-3-yl]-benzoic acid;
3-[5-(2,2-Difluoro-benzo[1,3]dioxol-5-yl)-[1,2,4]oxadiazol-3-yl]-benzoic acid;
4-Fluoro-3-[5-(4-fluoro-phenyl)-[1,2,4]oxadiazol-3-yl]-benzoic acid;
2-Fluoro-5-[5-(4-fluoro-phenyl)-[1,2,4]oxadiazol-3-yl]-benzoic acid;
3-[5-(4-Chloro-2-fluoro-phenyl)-[1,2,4]oxadiazol-3-yl]-benzoic acid;
3-[5-(4-Bromo-2-fluoro-phenyl)-[1,2,4]oxadiazol-3-yl]-benzoic acid;
3-[5-(3-Fluoro-biphenyl-4-yl)-[1,2,4]oxadiazol-3-yl]-benzoic acid;
3-{5-[3-(2-Chloro-phenyl)-5-methyl-isoxazol-4-yl]-[1,2,4]oxadiazol-3-yl}-benzoic acid;
3-[5-(4-Cyano-phenyl)-[1,2,4]oxadiazol-3-yl]-benzoic acid;
3-[5-(2-Fluoro-phenyl)-[1,2,4]oxadiazol-3-yl]-benzoic acid sodium salt;
3-[5-(4-Fluoro-phenyl)-[1,2,4]oxadiazol-3-yl]-benzoic acid methyl ester;
5-[5-(4-Fluoro-phenyl)-[1,2,4]oxadiazol-3-yl]-2-methoxy-benzoic acid;
3-[5-(4-Bromo-2-fluoro-phenyl)-[1,2,4]oxadiazol-3-yl]-benzoic acid;
3-[5-(3-Fluoro-biphenyl-4-yl)-[1,2,4]oxadiazol-3-yl]-benzoic acid;
3-[5-(6-Pyrrolidin-1-yl-pyridin-3-yl)-[1,2,4]oxadiazol-3-yl]-benzoic acid;
3-[5-(6-Morpholin-4-yl-pyridin-3-yl)-[1,2,4]oxadiazol-3-yl]-benzoic acid;
3-[5-(3,4,5,6-Tetrahydro-2H-[1,2']bipyridinyl-5'-yl)-[1,2,4]oxadiazol-3-yl]-benzoic acid;
3-[5-(2-Fluoro-6-hydroxy-phenyl)-[1,2,4]oxadiazol-3-yl]-benzoic acid;
3-[5-(2-Fluoro-phenyl)-[1,2,4]oxadiazol-3-yl]-benzoic acid methyl ester;
3-[5-(2-Fluoro-phenyl)-[1,2,4]oxadiazol-3-yl]-benzoic acid 2-methoxy-ethyl ester;
3-[5-(2-Fluoro-phenyl)-[1,2,4]oxadiazol-3-yl]-benzoic acid 2-(2-methoxy-ethoxy)-ethyl ester;
3-[5-(2-Fluoro-phenyl)-[1,2,4]oxadiazol-3-yl]-benzoic acid 2-[2-(2-methoxy-ethoxy)-ethoxy]-ethyl ester;
3-[5-(2-Fluoro-phenyl)-[1,2,4]oxadiazol-3-yl]-benzoic acid 2-{2-[2-(2-methoxy-ethoxy)-ethoxy]-ethoxy}-ethyl ester;
3-[5-(2-Fluoro-phenyl)-[1,2,4]oxadiazol-3-yl]-benzoic acid 2-(2-{2-[2-(2-methoxy-ethoxy)-ethoxy]-ethoxy}-ethoxy)-ethyl ester;
3-[5-(2-Fluoro-phenyl)-[1,2,4]oxadiazol-3-yl]-benzoic acid 2-[2-(2-{2-[2-(2-hydroxy-ethoxy)-ethoxy]-ethoxy}-ethoxy)-ethoxy]-ethyl ester;
3-[5-(4-Amino-phenyl)-[1,2,4]oxadiazol-3-yl]-benzoic acid;
3-[5-(4-Azido-phenyl)-[1,2,4]oxadiazol-3-yl]-benzoic acid; and
3-[5-(4-Benzyloxy-phenyl)-[1,2,4]oxadiazol-3-yl]-benzoic acid and pharmaceutically acceptable salts, hydrates, solvates, clathrates and stereoisomers thereof.

The compounds of formulas I and II and those listed above are herein referred to as "compounds of the invention". Exemplary compounds of the invention are depicted in Table 1 below.

TABLE 1
| Compound | | Compound Name | Activity |
|---|---|---|---|
| 01 | 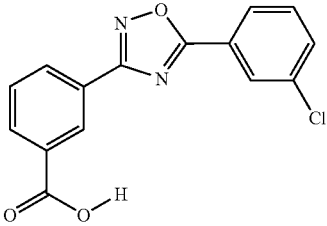 | 3-[5-(3-Chloro-phenyl)-[1,2,4]oxadiazol-3-yl]-benzoic acid | ***** |
| 02 | 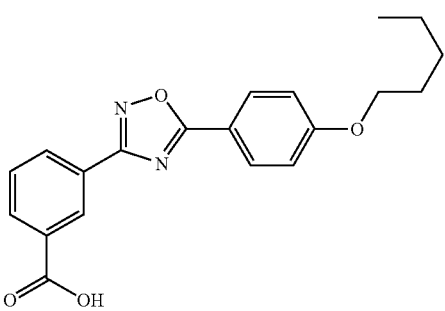 | 3-[5-(4-Pentyloxy-phenyl)-[1,2,4]oxadiazol-3-yl]-benzoic acid | *** |
| 03 | 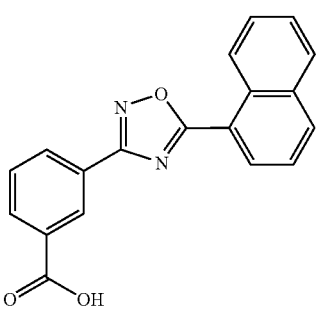 | 3-(5-Naphthalen-1-yl-[1,2,4]oxadiazol-3-yl)-benzoic acid | **** |
| 04 | 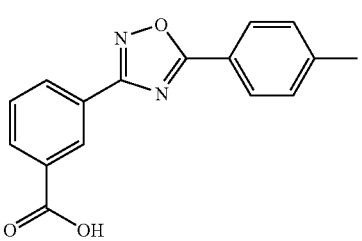 | 3-(5-p-Tolyl-[1,2,4]oxadiazol-3-yl)-benzoic acid | ***** |
| 05 | 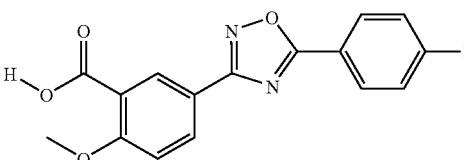 | 3-[5-(4-Fluoro-phenyl)-[1,2,4]oxadiazol-3-yl]-benzoic acid | ***** |
| 06 | 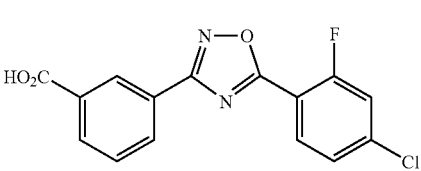 | 3-(5-Biphenyl-4-yl-[1,2,4]oxadiazol-3-yl)-benzoic acid | **** |

TABLE 1-continued

| Compound | | Compound Name | Activity |
|---|---|---|---|
| 07 | | 3-[5-(4-Isobutyl-phenyl)-[1,2,4]oxadiazol-3-yl]-benzoic acid | ** |
| 08 | | 3-(5-Phenyl-[1,2,4]oxadiazol-3-yl)-benzoic acid | ***** |
| 09 | | 3-(5-Cyclohexyl-[1,2,4]oxadiazol-3-yl)-benzoic acid | **** |
| 10 | | 3-[5-(3,4,5-Trimethoxy-phenyl)-[1,2,4]oxadiazol-3-yl]-benzoic acid | *** |
| 11 | | 3-[5-(4-Nitro-phenyl)-[1,2,4]oxadiazol-3-yl]-benzoic acid | **** |
| 12 | | 3-[5-(4-Methoxy-phhenyl)-[1,2,4]oxadiazol-3-yl]-benzoic acid | ***** |

TABLE 1-continued

| Compound | Compound Name | Activity |
|---|---|---|
| 13 | 3-[5-(o-tolyl)-[1,2,4]oxadiazol-3-yl]-benzoic acid | ***** |
| 14 | 3-(5-Benzo[1,3]dioxol-5-yl-[1,2,4]oxadiazol-3-yl)-benzoic acid | ***** |
| 15 | 3-(5-Isopropyl-[1,2,4]oxadiazol-3-yl)-benzoic acid | **** |
| 16 | 3-[5-(3,5-Bis-trifluoromethyl-phenyl)-[1,2,4]oxadiazol-3-yl]-benzoic acid | **** |
| 17 | 3-[5-(4-Trifluoromethyl-phenyl)-[1,2,4]oxadiazol-3-yl]-benzoic acid | ***** |
| 18 | 3-[5-(4-Dimethylamino-phenyl)-[1,2,4]oxadiazol-3-yl]-benzoic acid | **** |

TABLE 1-continued
| Compound | | Compound Name | Activity |
|---|---|---|---|
| 19 | 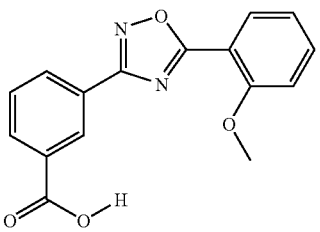 | 3-[5-(2-Methoxy-phenyl)-[1,2,4]oxadiazol-3-yl]-benzoic acid | *** |
| 20 | 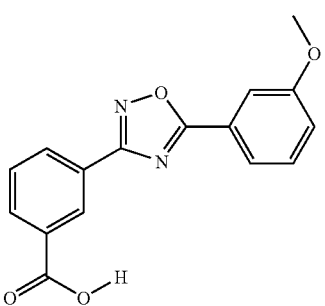 | 3-[5-(3-Methoxy-phenyl)-[1,2,4]oxadiazol-3-yl]-benzoic acid | **** |
| 21 | 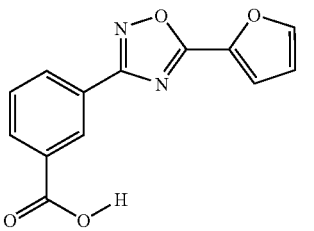 | 3-(5-Furan-2-yl-[1,2,4]oxadiazol-3-yl)-benzoic acid | **** |
| 22 | 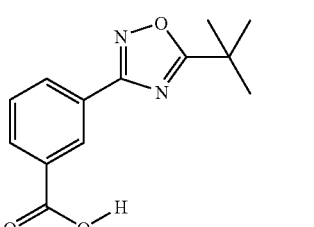 | 3-(5-tert-Butyl-[1,2,4]oxadiazol-3-yl)-benzoic acid | * |
| 23 | 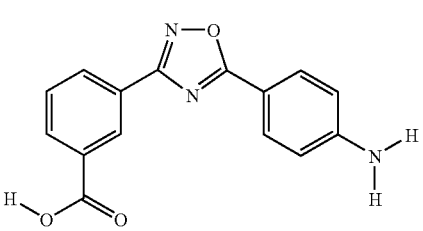 | 3-(5-Benzo[1,2,5]oxadiazol-5-yl-[1,2,4]oxadiazol-3-yl)-benzoic acid | **** |
| 24 | 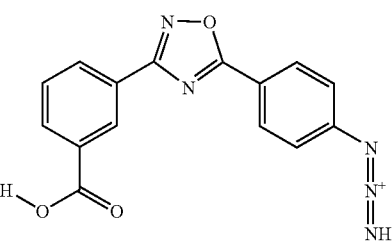 | 3-[5-(4-Chloromethyl-phenyl)-[1,2,4]oxadiazol-3-yl]-benzoic acid | ***** |

TABLE 1-continued
| Compound | | Compound Name | Activity |
|---|---|---|---|
| 25 | 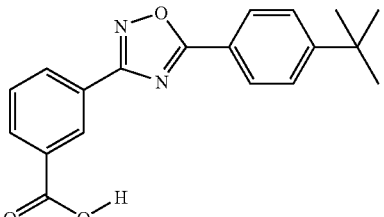 | 3-[5-(4-tert-Butyl-phenyl)-[1,2,4]oxadiazol-33-yl]-benzoic acid | ***** |
| 26 | 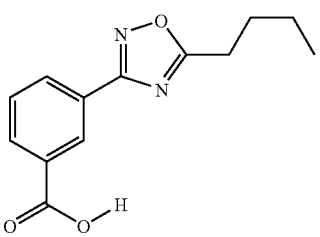 | 3-(5-Butyl-[1,2,4]oxadiazol-3-yl)-benzoic acid | **** |
| 27 | 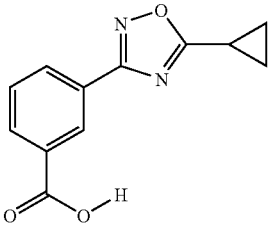 | 3-(5-Cyclopropyl-[1,2,4]oxadiazol-3-yl)-benzoic acid | **** |
| 28 | 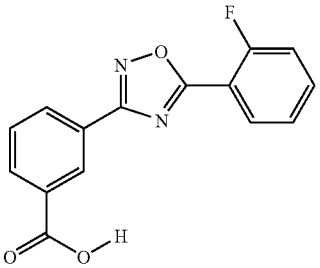 | 3-[5-(2-Fluoro-phenyl)-[1,2,4]oxadiazol-3-yl]-benzoic acid | ***** |
| 29 | 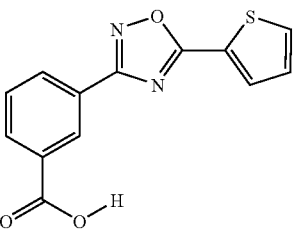 | 3-(5-Thiophen-2-yl-[1,2,4]oxadiazol-3-yl)-benzoic acid | **** |
| 30 | 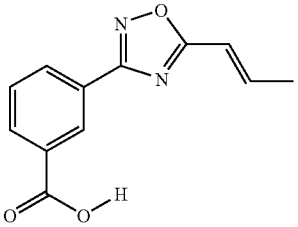 | 3-(5-Propenyl-[1,2,4]oxadiazol-3-yl)-benzoic acid | **** |

TABLE 1-continued

| Compound | | Compound Name | Activity |
|---|---|---|---|
| 31 | | 3-(5-Cyclopentyl-[1,2,4]oxadiazol-3-yl)-benzoic acid | **** |
| 32 | | 3-(5-Thiophen-2-ylmethyl-[1,2,4]oxadiazol-3-yl)-benzoic acid | **** |
| 33 | | 3-[5-(4-Chloro-benzyl)-[1,2,4]oxadiazol-3-yl]-benzoic acid | **** |
| 34 | | 3-[5-(4-Chloro-phenoxymethyl)-[1,2,4]oxadiazol-3-yl]-benzoic acid | **** |
| 35 | | 3-[5-(2-Trifluoromethyl-phenyl)-[1,2,4]oxadiazol-3-yl]-benzoic acid | **** |

TABLE 1-continued

| Compound | | Compound Name | Activity |
|---|---|---|---|
| 36 | | 3-[5-(2,6-Difluoro-phenyl)-[1,2,4]oxadiazol-3-yl]-benzoic acid | **** |
| 37 | | 3-[5-(3-Fluoro-phenyl)-[1,2,4]oxadiazol-3-yl]-benzoic acid | ***** |
| 38 | | 3-[5-(4-Ethyl-phenyl)-[1,2,4]oxadiazol-3-yl]-benzoic acid | ***** |
| 39 | | 3-[5-(3,4-Difluoro-phenyl)-[1,2,4]oxadiazol-3-yl]-benzoic acid | ***** |
| 40 | | 3-(5-m-Tolyl-[1,2,4]oxadiazol-3-yl)-benzoic acid | ***** |

TABLE 1-continued

| Compound | | Compound Name | Activity |
|---|---|---|---|
| 41 | | 3-[5-(4-Pyrrol-1-yl-phenyl)-[1,2,4]oxadiazol-3-yl]-benzoic acid | **** |
| 42 | | 3-(5-Benzyl-[1,2,4]oxadiazol-3-yl)-benzoic acid | *** |
| 43 | | 3-(5-Methoxymethyl-[1,2,4]oxadiazol-3-yl)-benzoic acid | * |
| 44 | | 3-[5-(3,5-Difluoro-phenyl)-[1,2,4]oxadiazol-3-yl]-benzoic acid | **** |
| 45 | | 3-[5-(1-Phenyl-propyl)-[1,2,4]oxadiazol-3-yl]-benzoic acid | * |
| 46 | | 3-[5-(2-Chloro-phenyl)-[1,2,4]oxadiazol-3-yl]-benzoic acid | ***** |

TABLE 1-continued

| Compound | | Compound Name | Activity |
|---|---|---|---|
| 47 | | 3-[5-(3-Trifluoromethoxy-phenytl)-[1,2,4]oxadiazol-3-yl]-benzoic acid | **** |
| 48 | | 3-[5-(4-Fluoro-beenzyl)-[1,2,4]oxadiazol-3-yl]-benzoic acid | **** |
| 49 | | 3-[5-(2,5-Dimethyl-furan-3-yl)-[1,2,4]oxadiazol-3-yl]-benzoic acid | **** |
| 50 | | 3-[5-(3-Methyl-thiophen-2-yl)-[1,2,4]oxadiazol-3-yl]-benzoic acid | ***** |
| 51 | | 3-[5-(3-Chloro-phenoxymethyl)-[1,2,4]oxadiazol-3-yl]-benzoic acid | ** |

TABLE 1-continued

| Compound | | Compound Name | Activity |
|---|---|---|---|
| 52 | | 3-(5-Isoxazol-5-yl-[1,2,4]oxadiazol-3-yl)-benzoic acid | ** |
| 53 | | 3-[5-(6-Chloro-pyridin-3-yl)-[1,2,4]oxadiazol-3-yl]-benzoic acid | **** |
| 54 | | 3-{5-[3-(2-Chloro-phenyl)-5-methyl-isoxazol-4-yl]-[1,2,4]oxadiazol-3-yl}-benzoic acid | |
| 55 | | 3-{5-[3-(2-Chloro-6-fluoro-phenyl)-5-methyl-isoxazol-4-yl]-[1,2,4]oxadiazol-3-yl}-benzoic acid | |
| 56 | | 3-(5-Cyclopentylmethyl-[1,2,4]oxadiazol-3-yl)-benzoic acid | *** |

TABLE 1-continued

| Compound | | Compound Name | Activity |
|---|---|---|---|
| 57 | | 3-[5-(2,4-Difluoro-phenyl)-[1,2,4]oxadiazol-3-yl]-benzoic acid | **** |
| 58 | | 3-(5-Pyridin-3-yl-[1,2,4]oxadiazol-3-yl)-benzoic acid | *** |
| 59 | | 3-(5-Pyridin-4-yl-[1,2,4]oxadiazol-3-yl)-benzoic acid | *** |
| 60 | | 3-(5-Cyclobutyl-[1,2,4]oxadiazol-3-yl)-benzoic acid | ** |
| 61 | | 3-[5-(4-Methoxy-benzyl)-[1,2,4]oxadiazol-3-yl]-benzoic acid | ** |

TABLE 1-continued
| Compound | | Compound Name | Activity |
|---|---|---|---|
| 62 | 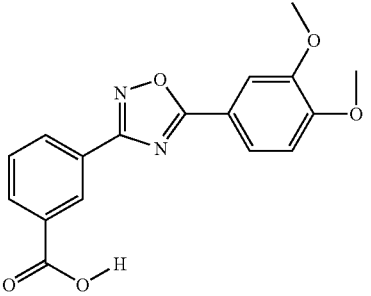 | 3-[5-(3,4-Dimethoxy-phenyl)-[1,2,4]oxadiazol-3-yl]-benzoic acid | **** |
| 63 | 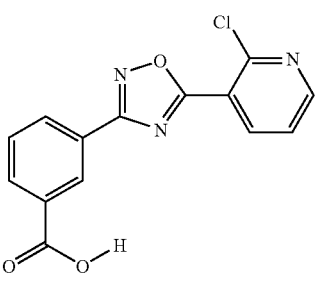 | 3-[5-(2-Chloro-pyridin-3-yl)-[1,2,4]oxadiazol-3-yl]-benzoic acid | **** |
| 64 | 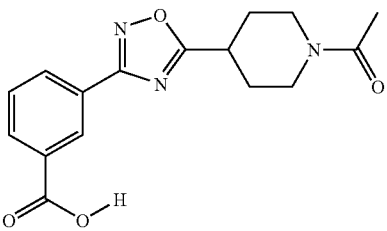 | 3-[5-(1-Acetyl-piperidin-4-yl)-[1,2,4]oxadiazol-3-yl]-benzoic acid | * |
| 65 | 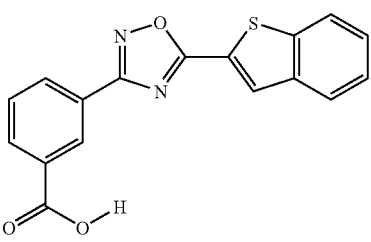 | 3-(5-Benzo[b]thiophen-2-yl-[1,2,4]oxadiazol-3-yl)-benzoic acid | ***** |
| 66 | 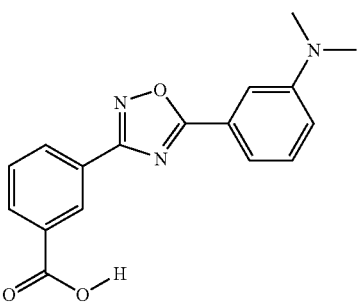 | 3-[5-(3-Dimethylamino-phenyl)-[1,2,4]oxadiazol-3-yl]-benzoic acid | **** |

TABLE 1-continued

| Compound | | Compound Name | Activity |
|---|---|---|---|
| 67 | | 3-[5-(2,3-Difluoro-phhenyl)-[1,2,4]oxadiazol-3-yl]-benzoic acid | **** |
| 68 | | 3-[5-(2-Fluoro-5-methyl-phenyl)-[1,2,4]oxadiazol-3-yl]-benzoic acid | *** |
| 69 | | 3-[5-(2-Methylsulfanyl-pyridin-3-yl)-[1,2,4]oxadiazol-3-yl]-benzoic acid | **** |
| 70 | | 3-[5-(2,2-Difluoro-benzo[1,3]dioxol-5-yl)-[1,2,4]oxadiazol-3-yl]-benzoic acid | *** |
| 71 | | 4-Fluoro-3-[5-(4-fluoro-phenyl)-[1,2,4]oxadiazol-3-yl]-benzoic acid | * |

TABLE 1-continued

| Compound | | Compound Name | Activity |
|---|---|---|---|
| 72 | | 2-Fluoro-5-[5-(4-fluoro-phenyl)-[1,2,4]oxadiazol-3-yl]-benzoic acid | *** |
| 73 | | 3-[5-(4-Chloro-2-fluoro-phenyl)-[1,2,4]oxadiazol-3-yl]-benzoic acid | **** |
| 74 | | 3-[5-(4-Bromo-2-fluoro-phenyl)-[1,2,4]oxadiazol-3-yl]-benzoic acid | *** |
| 75 | | 3-[5-(3-Fluoro-biphenyl-4-yl)-[1,2,4]oxadiazol-3-yl]-benzoic acid | **** |
| 76 | | 5-[5-(4-Fluoro-phenyl)-[1,2,4]oxadiazol-3-yl]-2-methoxy-benzoic acid | * |
| 77 | | 3-[5-(4-Cyano-phenyl)-[1,2,4]oxadiazol-3-yl]-benzoic acid | ***** |
| 78 | | 3-[5-(2-Fluoro-phenyl)-[1,2,4]oxadiazol-3-yl]-benzoic acid sodium salt | ***** |

TABLE 1-continued
| Compound | | Compound Name | Activity |
|---|---|---|---|
| 79 | 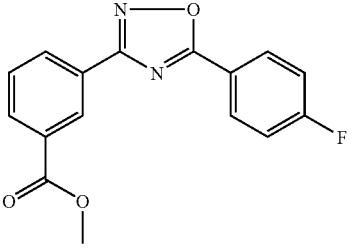 | 3-[5-(4-Fluoro-phenyl)-[1,2,4]oxadiazol-3-yl]-benzoic acid methyl ester | *** |
| 80 | 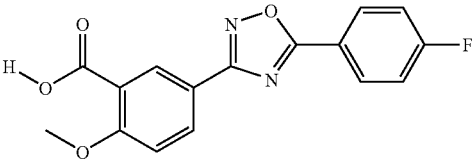 | 5-[5-(4-Fluoro-phenyl)-[1,2,4]oxadiazol-3-yl]-2-methoxy-benzoic acid | * |
| 81 | 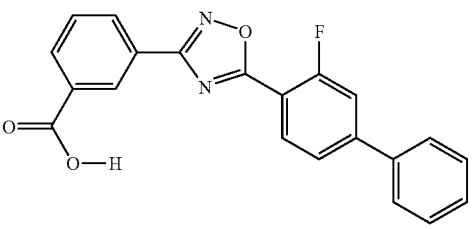 | 3-[5-(3-Fluoro-biphenyl-4-yl)-[1,2,4]oxadiazol-3-yl]-benzoic acid | ** |
| 82 | 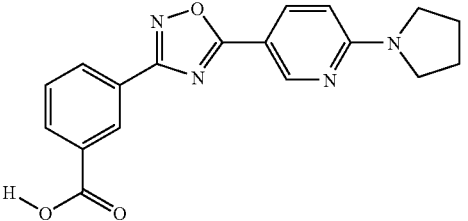 | 3-[5-(6-Pyrrolidin-1-yl-pyridin-3-yl)-[1,2,4]oxadiazol-3-yl]-benzoic acid | ***** |
| 83 | 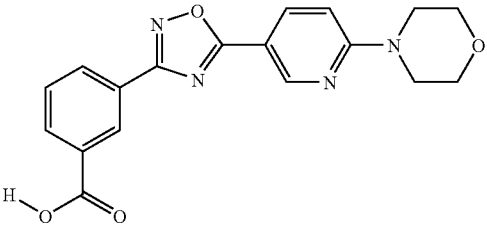 | 3-[5-(6-Morpholin-4-yl-pyridin-3-yl)-[1,2,4]oxadiazol-3-yl]-benzoic acid | **** |
| 84 | 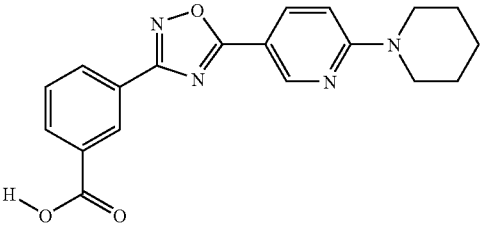 | 3-[5-(3,4,5,6-Tetrahydro-2H-[1,2']bipyridinyl-5'-yl)-[1,2,4]oxadiazol-3-yl]-benzoic acid | **** |

TABLE 1-continued

| Compound | | Compound Name | Activity |
|---|---|---|---|
| 85 | 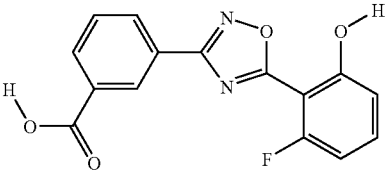 | 3-[5-(2-Fluoro-6-hydroxy-phenyl)-[1,2,4]oxadiazol-3-yl]-benzoic acid | ** |
| 86 | 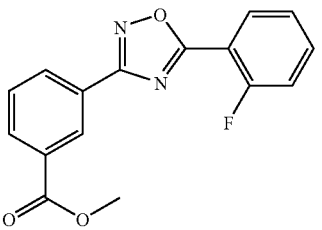 | 3-[5-(2-Fluoro-phenyl)-[1,2,4]oxadiazol-3-yl]-benzoic acid methyl ester | ** |
| 87 | 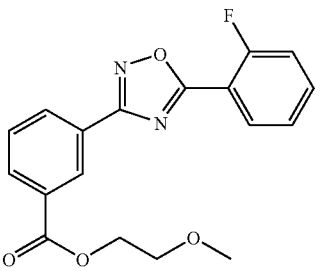 | 3-[5-(2-Fluoro-phenyl)-[1,2,4]oxadiazol-3-yl]-benzoic acid 2-methoxy-ethyl ester | *** |
| 88 | 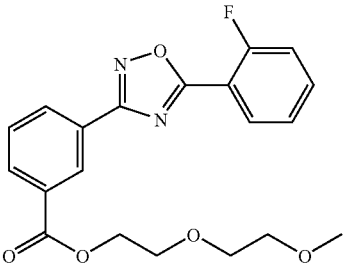 | 3-[5-(2-Fluoro-phenyl)-[1,2,4]oxadiazol-3-yl]-benzoic acid 2-(2-meethoxy-ethoxy)-ethyl ester | ** |
| 89 | 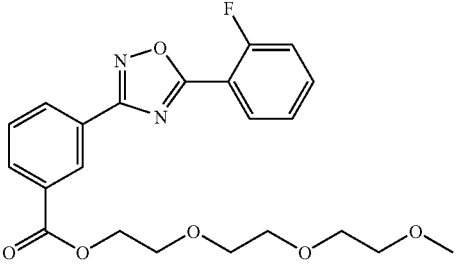 | 3-[5-(2-Fluoro-phenyl)-[1,2,4]oxadiazol-3-yl]-benzoic acid 2-[2-(2-meethoxy-ethoxy)-ethoxy]-ethyl ester | ** |
| 90 | 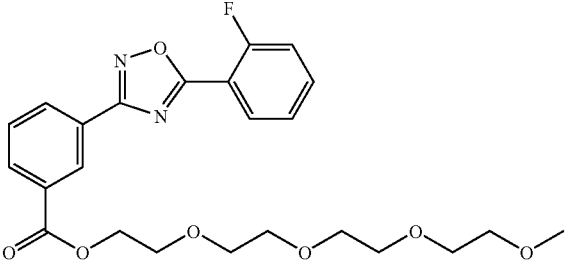 | 3-[5-(2-Fluoro-phenyl)-[1,2,4]oxadiazol-3-yl]-benzoic acid 2-{2-[2-(2-methoxy-ethoxy)-ethoxy]-ethoxy}-ethyl ester | ** |

TABLE 1-continued

| Compound | Compound Name | Activity |
|---|---|---|
| 91 | 3-[5-(2-Fluoro-phenyl)-[1,2,4]oxadiazol-3-yl]-benzoic acid 2-{2-[2-(2-methoxy-ethoxy)-ethoxy]-ethoxy}-ethoxy)-ethyl ester | *** |
| 92 | 3-[5-(2-Fluoro-phenyl)-[1,2,4]oxadiazol-3-yl]-benzoic acid 2-[2-(2-{2-[2-(2-hydroxy-eethoxy)-ethoxy]-ethoxy}-ethoxy)-ethoxy]-ethyl ester | *** |
| 93 | 3-[5-(4-Amino-phenyl)-[1,2,4]oxadiazol-3-yl]-benzoic acid | **** |
| 94 | 3-[5-(4-Azido-phenyl)-[1,2,4]oxadiazol-3-yl]-benzoic acid | ***** |
| 95 | 3-[5-(4-Benzyloxy-phenyl)-[1,2,4]oxadiazol-3-yl]-benzoic acid | * |

Activity measurements in Table I were performed in a cell-based luciferase reporter assay (as described in Section 4.2) comprising a luciferase reporter construct containing a UGA premature termination codon that was stably transfected in 293T Human Embryonic Kidney cells. A small molecule, 3-[3-(4-Isopropyl-phenyl)-2,5-dioxo-imidazolidin-1-yl]-benzoic acid, known to allow readthrough of premature termination codons was used was used as an internal standard. Activity measurements are based on the qualitative relation between the minimum concentration of compound required to produce a given protein in a cell (potency) and the maximum amount of protein produced by the cell (efficacy). Potency and efficacy activities are ranked as either extremely high, very high or significant. The combination of these activities is used to determine the activity ranking. Compounds which were found to have both extremely high potency and extremely high efficacy of protein synthesis are classified as "***". Compounds which were found to have extremely high potency of protein synthesis and very high efficacy were classified as "". Compounds which were found to have very high potency of protein synthesis and extremely high efficacy were classified as "". Compounds which were found to have both very high potency and very high efficacy of protein synthesis are classified as "*". Compounds which were found to have very high potency of protein synthesis and significant efficacy were classified as "". Compounds which were found to have significant potency of protein synthesis and very high efficacy were classified as "". Similarly, compounds which were found to have significant potency and efficacy of protein synthesis were classified as "*" (see table below).

| Potency | Efficacy | Ranking |
| --- | --- | --- |
| Extremely high | Extremely high | ***** |
| Extremely high | Very high | **** |
| Very high | Extremely high | **** |
| Very high | Very high | *** |
| Very high | Significant | ** |
| Significant | Very high | ** |
| Significant | Significant | * |

Compounds having less than significant potency or efficacy of protein synthesis or both in the cell-based luciferase assay were classified with no asterisks. Nevertheless, these compounds are believed to have utility in the in vivo methods of the invention.

The present invention encompasses the in vitro or in vivo use of a compound of the invention, and the incorporation of a compound of the invention into pharmaceutical compositions and single unit dosage forms useful in the treatment and prevention of a variety of diseases and disorders. Specific diseases and disorders include those ameliorated by the suppression of a nonsense mutation in messenger RNA.

Pharmaceutical compositions including dosage forms of the invention, which comprise a compound of the invention or a pharmaceutically acceptable polymorph, prodrug, salt, clathrate, solvate or hydrate thereof, can be used in the methods of the invention.

Without being limited by theory, it is believed that a compound of the invention can modulate premature translation termination and/or nonsense-mediated mRNA decay. Consequently, a first embodiment of the invention relates to a method of modulating premature translation termination and/or nonsense-mediated mRNA decay comprising contacting a cell exhibiting a nonsense mutation with an effective amount of a compound of the invention, or a pharmaceutically acceptable prodrug, metabolite, polymorph, salt, solvate, hydrate, or clathrate thereof. In a particular embodiment, the invention relates to a method of inducing nonsense suppression comprising contacting a cell exhibiting a nonsense mutation with an effective amount of a compound of the invention, or a pharmaceutically acceptable prodrug, metabolite, polymorph, salt, solvate, hydrate, or clathrate thereof.

4.2 Biological Assays and Animal Studies

Compounds that modulate premature translation termination and/or nonsense-mediated mRNA decay can be identified by a number of techniques. For example, methods for screening compounds that modulate the post-transcriptional expression of any gene with a premature translation stop codon are described in International Patent Publication No. WO 01/44516 A2, incorporated herein in its entirety by reference. In a preferred embodiment, a mRNA with a premature termination codon is translated in vitro and is used to screen a library of test compounds. In a preferred embodiment, the mRNA with a premature termination codon is a reporter gene with a premature termination codon.

Two assays were developed for use in high throughput screens to identify small molecules that promote nonsense suppression. Each assay utilized luciferase because it is a functional reporter gene assay (light is only produced if the protein is functional) and it is extremely sensitive (Light intensity is proportional to luciferase concentration in the nM range). The first assay is a cell-based luciferase reporter assay and the second is a biochemical assay consisting of rabbit reticulocyte lysate and a nonsense-containing luciferase reporter mRNA. In the cell-based assay, a luciferase reporter construct containing a UGA premature termination codon was stably transfected in 293T Human Embryonic Kidney cells. In the biochemical assay, mRNA containing a UGA premature termination codon was used as a reporter in an in vitro translation reaction using rabbit reticulocyte lysate supplemented with tRNA, hemin, creatine kinase, amino acids, KOAc, Mg(OAc)2, and creatine phosphate. Translation of the mRNA was initiated within a virus derived leader sequence, which significantly reduced the cost of the assay because capped RNA was not required. Synthetic mRNA was prepared in vitro using the T7 promoter and the MegaScript in vitro transcription kit (Ambion). In both of the biochemical and cell-based assays, addition of a small molecule known to allow readthrough of premature termination codons, 3-[3-(4-Isopropyl-phenyl)-2,5-dioxo-imidazolidin-1-yl]-benzoic acid, resulted in increased luciferase activity and was, therefore, used as an internal standard.

Animal model systems can also be used to demonstrate the safety and efficacy of compounds of formula I or II. The compounds of formula I or II can be tested for biological activity using animal models for a disease, condition, or syndrome of interest. These include animals engineered to contain the target RNA element coupled to a functional readout system, such as a transgenic mouse.

Examples of animal models for cystic fibrosis include, but are not limited to, cftr(−/−) mice (see, e.g., Freedman et al., 2001, Gastroenterology 121(4):950-7), cftr(tm1HGU/tm1HGU) mice (see, e.g., Bernhard et al., 2001, Exp Lung Res 27(4):349-66), CFTR-deficient mice with defective cAMP-mediated Cl(−) conductance (see, e.g., Stotland et al., 2000, Pediatr Pulmonol 30(5):413-24), and C57BL/6-Cftr (m1UNC)/Cftr(m1UNC) knockout mice (see, e.g., Stotland et al., 2000, Pediatr Pulmonol 30(5):413-24).

Examples of animal models for muscular dystrophy include, but are not limited to, mouse, hamster, cat, dog, and C. elegans. Examples of mouse models for muscular dystrophy include, but are not limited to, the dy−/− mouse (see, e.g., Connolly et al., 2002, J Neuroimmunol 127(1-2):80-7), a muscular dystrophy with myositis (mdm) mouse mutation (see, e.g., Garvey et al., 2002, Genomics 79(2): 146-9), the mdx mouse (see, e.g., Nakamura et al., 2001, Neuromuscul Disord 11(3):251-9), the utrophin-dystrophin knockout (dko) mouse (see, e.g., Nakamura et al., 2001, Neuromuscul Disord 11(3):251-9), the dy/dy mouse (see, e.g., Dubowitz et al., 2000, Neuromuscul Disord 10(4-5):292-8), the mdx(Cv3) mouse model (see, e.g., Pillers et al., 1999, Laryngoscope 109(8):1310-2), and the myotonic ADR-MDX mutant mice (see, e.g., Kramer et al., 1998, Neuromuscul Disord 8(8):542-50). Examples of hamster models for muscular dystrophy include, but are not limited to, sarcoglycan-deficient hamsters (see, e.g., Nakamura et al., 2001, Am J Physiol Cell Physiol 281(2):C690-9) and the BIO 14.6 dystrophic hamster (see, e.g., Schlenker & Burbach, 1991, J Appl Physiol 71(5):1655-62). An example of a feline model for muscular dystrophy includes, but is not limited to, the hypertrophic feline muscular dystrophy model (see, e.g., Gaschen & Burgunder, 2001, Acta Neuropathol (Berl) 101(6):591-600). Canine models for muscular dystrophy include, but are not limited to, golden retriever muscular dystrophy (see, e.g., Fletcher et al., 2001, Neuromuscul Disord 11(3):239-43) and canine X-linked muscular dystrophy (see, e.g., Valentine et al., 1992, Am J Med Genet 42(3):352-6). Examples of *C. elegans* models for muscular dystrophy are described in Chamberlain & Benian, 2000, Curr Biol 10(21):R795-7 and Culette & Sattelle, 2000, Hum Mol Genet 9(6):869-77.

Examples of animal models for familial hypercholesterolemia include, but are not limited to, mice lacking functional LDL receptor genes (see, e.g., Aji et al., 1997, Circulation 95(2):430-7), Yoshida rats (see, e.g., Fantappie et al., 1992, Life Sci 50(24): 1913-24), the JCR:LA-cp rat (see, e.g., Richardson et al., 1998, Atherosclerosis 138(1):135-46), swine (see, e.g., Hasler-Rapacz et al., 1998, Am J Med Genet 76(5): 379-86), and the Watanabe heritable hyperlipidaemic rabbit (see, e.g., Tsutsumi et al., 2000, Arzneimittelforschung 50(2): 118-21; Harsch et al., 1998, Br J Pharmacol 124(2):227-82; and Tanaka et al., 1995, Atherosclerosis 114(1):73-82).

An example of an animal model for human cancer in general includes, but is not limited to, spontaneously occurring tumors of companion animals (see, e.g., Vail & MacEwen, 2000, Cancer Invest 18(8):781-92). Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCRbeta and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3): 1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63). An example of an animal model for neurofibromatosis includes, but is not limited to, mutant NF1 mice (see, e.g., Cichowski et al., 1996, Semin Cancer Biol 7(5):291-8). Examples of animal models for retinoblastoma include, but are not limited to, transgenic mice that expression the simian virus 40 T antigen in the retina (see, e.g., Howes et al., 1994, Invest Ophthalmol Vis Sci 35(2):342-51 and Windle et al, 1990, Nature 343 (6259):665-9) and inbred rats (see, e.g., Nishida et al., 1981, Curr Eye Res 1(1):53-5 and Kobayashi et al., 1982, Acta Neuropathol (Berl) 57(2-3):203-8). Examples of animal models for Wilm's tumor include, but are not limited to, a WT1 knockout mice (see, e.g., Scharnhorst et al., 1997, Cell Growth Differ 8(2):133-43), a rat subline with a high incidence of neuphroblastoma (see, e.g., Mesfin & Breech, 1996, Lab Anim Sci 46(3):321-6), and a Wistar/Furth rat with Wilms' tumor (see, e.g., Murphy et al., 1987, Anticancer Res 7(4B):717-9).

Examples of animal models for retinitis pigmentosa include, but are not limited to, the Royal College of Surgeons ("RCS") rat (see, e.g., Vollrath et al., 2001, Proc Natl Acad Sci USA 98(22); 12584-9 and Hanitzsch et al., 1998, Acta Anat (Basel) 162(2-3):119-26), a rhodopsin knockout mouse (see, e.g., Jaissle et al., 2001, Invest Ophthalmol Vis Sci 42(2):506-13), and Wag/Rij rats (see, e.g., Lai et al., 1980, Am J Pathol 98(1):281-4).

Examples of animal models for cirrhosis include, but are not limited to, $CCl_4$-exposed rats (see, e.g., Kloehn et al., 2001, Horm Metab Res 33(7):394-401) and rodent models instigated by bacterial cell components or colitis (see, e.g., Vierling, 2001, Best Pract Res Clin Gastroenterol 15(4):591-610).

Examples of animal models for hemophilia include, but are not limited to, rodent models for hemophilia A (see, e.g., Reipert et al., 2000, Thromb Haemost 84(5):826-32; Jarvis et al.,. 1996, Thromb Haemost 75(2):318-25; and Bi et al., 1995, Nat Genet 10(1): 119-21), canine models for hemophilia A (see, e.g., Gallo-Penn et al., 1999, Hum Gene Ther 10(11): 1791-802 and Connelly et al, 1998, Blood 91(9);3273-81), murine models for hemophilia B (see, e.g., Snyder et al., 1999, Nat Med 5(1):64-70; Wang et al., 1997, Proc Natl Acad Sci USA 94(21):11563-6; and Fang et al., 1996, Gene Ther 3(3):217-22), canine models for hemophilia B (see, e.g., Mount et al., 2002, Blood 99(8):2670-6; Snyder et al., 1999, Nat Med 5(1):64-70; Fang et al., 1996, Gene Ther 3(3):217-22); and Kay et al., 1994, Proc Natl Acad Sci USA 91(6): 2353-7), and a rhesus macaque model for hemophilia B (see, e.g., Lozier et al., 1999, Blood 93(6):1875-81).

Examples of animal models for von Willebrand disease include, but are not limited to, an inbred mouse strain RIIIS/J (see, e.g., Nichols et al., 1994, 83(11):3225-31 and Sweeney et al., 1990, 76(11):2258-65), rats injected with botrocetin (see, e.g., Sanders et al., 1988, Lab Invest 59(4):443-52), and porcine models for von Willebrand disease (see, e.g., Nichols et al., 1995, Proc Natl Acad Sci USA 92(7):2455-9; Johnson & Bowie, 1992, J Lab Clin Med 120(4):553-8); and Brinkhous et al., 1991, Mayo Clin Proc 66(7):733-42).

Examples of animal models for b-thalassemia include, but are not limited to, murine models with mutations in globin genes (see, e.g., Lewis et al., 1998, Blood 91(6):2152-6; Raja et al., 1994, Br J Haematol 86(1):156-62; Popp et al., 1985, 445:432-33; and Skow et al., 1983, Cell 34(3):1043-52).

Examples of animal models for kidney stones include, but are not limited to, genetic hypercalciuric rats (see, e.g., Bushinsky et al., 1999, Kidney Int 55(1):234-43 and Bushinsky et al., 1995, Kidney Int 48(6):1705-13), chemically treated rats (see, e.g., Grases et al., 1998, Scand J Urol Nephrol 32(4): 261-5; Burgess et al., 1995, Urol Res 23(4):239-42; Kumar et al., 1991, J Urol 146(5):1384-9; Okada et al., 1985, Hinyokika Kiyo 31(4):565-77; and Bluestone et al., 1975, Lab Invest 33(3):273-9), hyperoxaluric rats (see, e.g., Jones et al., 1991, J Urol 145(4):868-74), pigs with unilateral retrograde flexible nephroscopy (see, e.g., Seifmah et al., 2001, 57(4): 832-6), and rabbits with an obstructed upper urinary tract (see, e.g., Itatani et al., 1979, Invest Urol 17(3):234-40).

Examples of animal models for ataxia-telangiectasia include, but are not limited to, murine models of ataxia-telangiectasia (see, e.g., Barlow et al., 1999, Proc Natl Acad Sci USA 96(17):9915-9 and Inoue et al., 1986, Cancer Res 46(8):3979-82).

Examples of animal models for lysosomal storage diseases include, but are not limited to, mouse models for mucopolysaccharidosis type VII (see, e.g., Brooks et al., 2002, Proc Natl Acad Sci USA. 99(9):6216-21; Monroy et al., 2002, Bone 30(2):352-9; Vogler et al., 2001, Pediatr Dev Pathol. 4(5):421-33; Vogler et al., 2001, Pediatr Res. 49(3):342-8; and Wolfe et al., 2000, Mol Ther. 2(6):552-6), a mouse model for metachromatic leukodystrophy (see, e.g., Matzner et al., 2002, Gene Ther. 9(1):53-63), a mouse model of Sandhoff disease (see, e.g., Sango et al., 2002, Neuropathol Appl Neurobiol. 28(1):23-34), mouse models for mucopolysaccharidosis type III A (see, e.g., Bhattacharyya et al., 2001, Glycobiology 11(1):99-10 and Bhaumik et al., 1999, Glycobiology 9(12):1389-96.), arylsulfatase A (ASA)-deficient mice (see, e.g., D'Hooge et al., 1999, Brain Res. 847(2):352-6 and D'Hooge et al, 1999, Neurosci Lett. 273(2):93-6); mice with an aspartylglucosaminuria mutation (see, e.g., Jalanko et al., 1998, Hum Mol Genet. 7(2):265-72); feline models of mucopolysaccharidosis type VI (see, e.g., Crawley et al., 1998, J Clin Invest. 101(1):109-19 and Norrdin et al., 1995, Bone 17(5):485-9); a feline model of Niemann-Pick disease type C (see, e.g., March et al., 1997, Acta Neuropathol (Berl). 94(2): 164-72); acid sphingomyelinase-deficient mice (see, e.g., Otterbach & Stoffel, 1995, Cell 81(7):1053-6), and bovine mannosidosis (see, e.g., Jolly et al., 1975, Birth Defects Orig Arctic Ser. 11(6):273-8).

Examples of animal models for tuberous sclerosis ("TSC") include, but are not limited to, a mouse model of TSC1 (see, e.g., Kwiatkowski et al., 2002, Hum Mol Genet. 11(5):525-34), a Tsc1 (TSC1 homologue) knockout mouse (see, e.g., Kobayashi et al., 2001, Proc Natl Acad Sci USA. 2001 Jul. 17; 98(15):8762-7), a TSC2 gene mutant(Eker) rat model (see, e.g., Hino 2000, Nippon Rinsho 58(6):1255-61; Mizuguchi et al., 2000, J Neuropathol Exp Neurol. 59(3):188-9; and Hino et al., 1999, Prog Exp Tumor Res. 35:95-108); and Tsc2(+/−) mice (see, e.g., Onda et al., 1999, J Clin Invest. 104(6): 687-95).

4.3 Synthesis and Preparation

The compounds of the invention can be obtained via standard, well-known synthetic methodology, see e.g. March, J. *Advanced Organic Chemistry; Reactions Mechanisms, and Structure,* 4th ed., 1992. Starting materials useful for preparing the compounds of the invention and intermediates therefor, are commercially available or can be prepared from commercially available materials using known synthetic methods and reagents.

Compounds of Formulas I or II can be synthesized using the synthesis depicted in schemes A and B below. The compounds of the present invention may be prepared by the methods discussed in the following section.

Compounds of formula I may be prepared using the methodology depicted in Scheme A.

Scheme A.

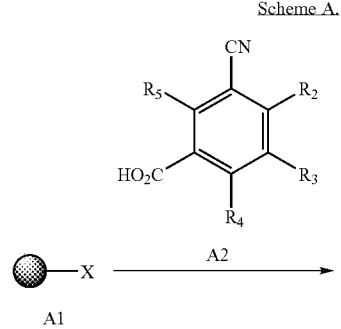

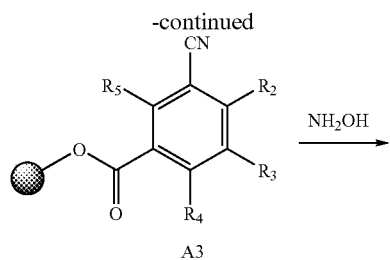

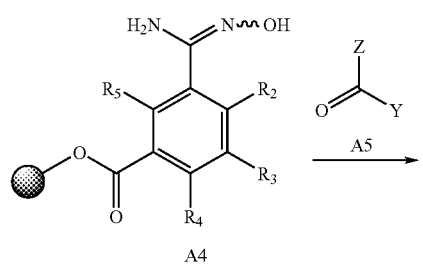

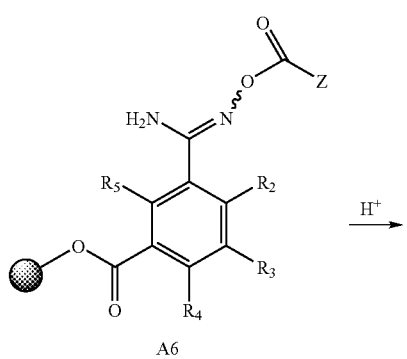

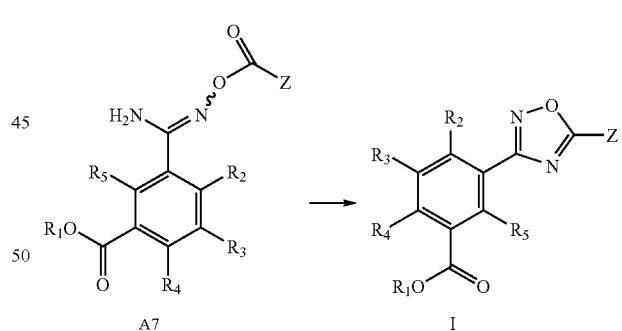

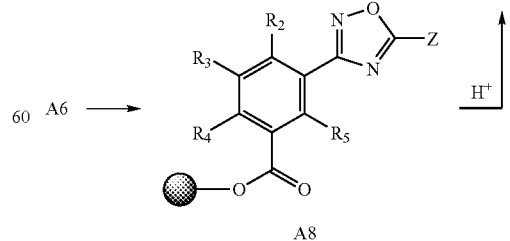

Commercially available, acid-labile resin A1 such as trityl resin, 2-chlorotrityl chloride resin, phenylacetamidomethyl (PAM) resin, and p-alkoxybenzyl alcohol resin can be used in this invention. The coupling of benzoic acid compound A2 and trityl resin (here X=2-chlrotrityl chloride) can be performed in a suitable solvent such as dichloromethane, dimethylformamide, toluene in the presence of a tertiary amine reagent such as diisopropylethylamine or triethylamine. In an alternative method, the acylated resin A3 is conveniently prepared using standard ester linkage formation conditions using diisopropylcarbodiimide (for phenylacetamidomethyl resin and p-alkoxybenzyl alcohol resin) or equivalents such as benzotriazole-1-yl-oxy-tris-pyrrolidino-phosphonium hexafluorophosphate(PyBOP), bromo-tris-pyrrolidino-phosphonium hexafluorophosphate (PyBrOP), 1-ethyl-3-(3-dimethylaminopropyl)carbodiimide hydrochloride (EDC) without or with diisopropylethylamine in dimethylformamide. The resin-bound cyanobenzoic ester can be treated with hydroxylamine in an inert solvent such as ethanol, tetrahydrofuran, dioxane and dimethylformamide or mixtures with or without diisopropylethylamine to afford the hydroxyamidine compound A4. The hydroxyamidine resin A4 can be used as a common linker for the synthesis of 1,2,4-oxadiazole library compounds with variation of the rest of the compound of structure I as shown in Scheme A. The resin-bound hydroxyamidine compound is acylated with a reagent A5, wherein the group Y represents some leaving groups, such as halo, imidazoyl, p-nitrophenol, etc. in the presence of a base reagent, such as diisopropylethylamine or triethylamine, in an inert solvent such as dichloromethane, tetrahydrofuran and dimethylformamide or mixtures. An alternative method, the acylation is conveniently carried out with a reagent 5, wherein the group Y represents hydroxy, using diisopropylcarbodiimide or equivalents such as benzotriazole-1-yl-oxy-tris-pyrrolidino-phosphonium hexafluorophosphate, bromo-tris-pyrrolidino-phosphonium hexafluorophosphate, 1-ethyl-3-(3-dimethylaminopropyl)carbodiimide hydrochloride without or with diisopropylethylamine in dimethylformamide. The resin-bound acylated compound A6 is cleaved under acidic conditions such as 2 molar trifluoroacetic acid in dichloromethane, or 3 molar acetic acid in dichloromethane, to afford the desired compound A7. A ring-closure reaction on free acid compound A7 can be effected by the reflux in an inert solvent such as toluene, tetrahydrofuran, dioxane and dimethylformamide or mixtures with or without a base reagent such as diisopropylethylamine, triethylamine or tetrabutylammonium fluoride to afford the 1,2,4-oxdiazole compound I. An alternative ring-closure reaction can be performed by dehydrocyclization of the resin-bound compound A6 (Scheme A). This transformation can be accomplished with or without a base reagent such as triethylamine, diisopropylethylamine, or tetrabutylammonium fluoride in an inert solvent such as toluene, tetrahydrofuran, dioxane and dimethylformamide or mixtures. Temperatures of the reaction range from ambient to reflux of the solvent.

The solid phase chemistry described above can be applied to the solution phase synthesis of compounds of structure I. This is described in Scheme B, below.

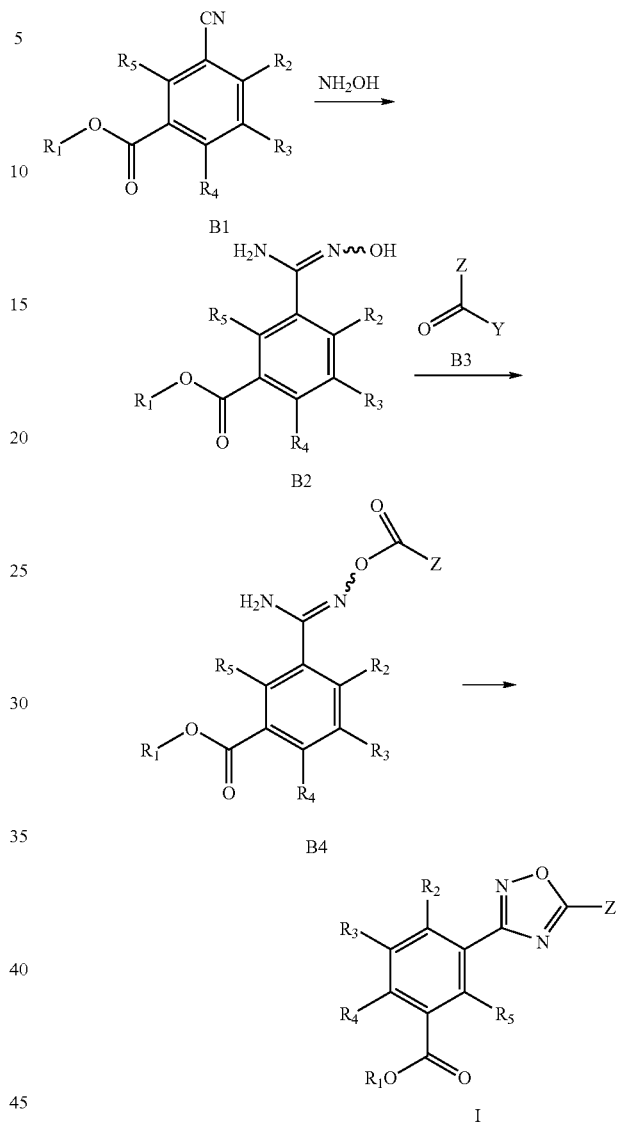

The cyano compound B1 is hydoxyamidinated with hydoxyl amine. This reaction is usually performed in the presence of a base reagent, such as triethyl amine, potassium carbonate or diisopropylethylamine, in a solvent such as methanol, ethanol, tert-butanol, tetrahydrofuan or dimethylformaide, and temperatures ranging from ambient to the reflux temperature of the chosen solvent. The hydroxyamidine compound B2 is acylated with a reagent B3, wherein the group Y represents some leaving groups, such as halo, imidazoyl, p-nitrophenol, etc. The reaction is usually carried out with a base reagent, such as triethyl amine or diisopropylethylamine, in a solvent such as dichloromethane, tetahydrofuan or dimethylformaide. An alternative method, the acylation is conveniently carried out under usual ester linkage formation reactions, wherein the group Y represents hydroxy, using diisopropylcarbodiimide or equivalents such as benzotriazole-1-yl-oxy-tris-pyrrolidino-phosphonium hexafluorophosphate, bromo-tris-pyrrolidino-phosphonium hexafluorophosphate, 1-ethyl-3-(3-dimethylaminopropyl)

carbodiimide hydrochloride without or with diisopropylethylamine. The ring-closure on the acylated compound B4 can be accomplished with or without a base reagent such as triethyl amine or diisopropylethylamine, in a solvent such as dichloromethane, tetrahydrofuran, toluene or dimethylformaide, and temperatures ranging from ambient to the reflux temperature of the chosen solvent.

4.4 Methods of Use

The invention encompasses methods of treating and preventing diseases or disorders ameliorated by the suppression of premature translation termination and/or nonsense-mediated mRNA decay in a patient which comprise administering to a patient in need of such treatment or prevention a therapeutically effective amount of a compound of the invention, or a pharmaceutically acceptable prodrug, solvate, metabolite, polymorph, salt, solvate, hydrate, or clathrate thereof.

In one embodiment, the present invention encompasses the treatment or prevention of any disease that is associated with a gene exhibiting premature translation termination and/or nonsense-mediated mRNA decay. In one embodiment, the disease is due, in part, to the lack of expression of the gene resulting from a premature stop codon. Specific examples of genes which may exhibit premature translation termination and/or nonsense-mediated mRNA decay and diseases associated with premature translation termination and/or nonsense-mediated mRNA decay are found in U.S. Patent Application No. 60/390,747, titled: Methods For Identifying Small Molecules That Modulate Premature Translation Termination And Nonsense Mediated mRNA Decay, filed Jun. 21, 2002, which is incorporated herein by reference in its entirety.

Diseases ameliorated by the suppression of premature translation termination and/or nonsense-mediated mRNA decay include, but are not limited to: a genetic disease, cancer, an autoimmune disease, a blood disease, a collagen disease, diabetes, a neurodegenerative disease, a proliferative disease, a cardiovascular disease, a pulmonary disease, an inflammatory disease or central nervous system disease.

Specific genetic diseases within the scope of the methods of the invention include, but are not limited to, amyloidosis, hemophilia, Alzheimer's disease, Tay Sachs disease, atherosclerosis, giantism, dwarfism, hypothyroidism, hyperthyroidism, aging, obesity, Parkinson's disease, Niemann Pick's disease, cystic fibrosis, muscular dystrophy, heart disease, kidney stones, ataxia-telangiectasia, familial hypercholesterolemia, retinitis pigmentosa, lysosomal storage disease, tuberous sclerosis, Duchenne muscular dystrophy, and Marfan syndrome. Both solid tumor and other cancers are included within the methods of the invention.

In another embodiment, the genetic disease is an autoimmune disease. In a preferred embodiment, the autoimmune disease is rheumatoid arthritis or graft versus host disease.

In another embodiment, the genetic disease is a blood disease. In a preferred embodiment, the blood disease is hemophilia, Von Willebrand disease, ataxia-telangiectasia, b-thalassemia or kidney stones.

In another embodiment, the genetic disease is a collagen disease. In a embodiment, the collagen disease is osteogenesis imperfecta or cirrhosis.

In another embodiment, the genetic disease is diabetes.

In another embodiment, the genetic disease is an inflammatory disease. In a preferred embodiment, the inflammatory disease is arthritis.

In another embodiment, the genetic disease is a central nervous system disease. In one embodiment the central nervous system disease is a neurodegenerative disease. In a preferred embodiment, the central nervous system disease is multiple sclerosis, muscular dystrophy, Duchenne muscular dystrophy, Alzheimer's disease, Tay Sachs disease, late infantile neuronal ceroid lipofuscinosis (LINCL) or Parkinson's disease.

In another embodiment, the genetic disease is cancer. In a preferred embodiment, the cancer is of the head and neck, eye, skin, mouth, throat, esophagus, chest, bone, lung, colon, sigmoid, rectum, stomach, prostate, breast, ovaries, kidney, liver, pancreas, brain, intestine, heart or adrenals.

In another preferred embodiment, the cancer is associated with tumor suppressor genes (see e.g. Garinis et al. 2002, Hum Gen 111:115-117; Meyers et al. 1998, Proc. Natl. Acad. Sci. USA, 95: 15587-15591; Kung et al. 2000, Nature Medicine 6(12): 1335-1340. Such tumor suppressor genes include, but are not limited to, APC, ATM, BRAC1, BRAC2, MSH1, pTEN, Rb and p53.

In a particularly preferred embodiment, the tumor suppressor gene is the p53 gene. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2): 114-8; Finkelstein et al., 1998, Mol Diagn. 3(1):37-41; Kajiyama et al., 1998, Dis Esophagus. 11(4):279-83; Kawamura et al., 1999, Leuk Res. 23(2): 115-26; Radig et al., 1998, Hum Pathol. 29(11):1310-6; Schuyer et al., 1998, Int J Cancer 76(3):299-303; Wang-Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100(1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8):1342-9; McIntyre et al., 1994, J Clin Oncol. 12(5): 925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference in their entireties). Any disease associated with a p53 gene encoding a premature translation codon including, but not limited to, the nonsense mutations described in the references cited above, can be treated or prevented by compounds of formula I or II without being limited by theory these compounds mediate premature translation termination and/or nonsense-mediated mRNA decay.

In other embodiments, diseases to be treated or prevented by administering to a patient in need thereof an effective amount of a compound of formula I include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, or multiple myeloma. See e.g., *Harrison's Principles of Internal Medicine,* Eugene Braunwald et al., eds., pp. 491-762 (15th ed. 2001).

In a preferred embodiment, the invention encompasses a method of treating or preventing a disease ameliorated by modulation of premature translation termination and/or nonsense-mediated mRNA decay, or ameliorating one or more symptoms associated therewith comprising contacting a cell with an effective amount of a compound of formula I or II. Cells encompassed by the present methods include animal cells, mammalian cells, bacterial cells, plant cells and virally infected cells. In one embodiment, the nonsense codon was present in the progenitor DNA. In another embodiment, the nonsense codon resulted from mutagenesis.

In certain embodiments, a compound of formula I or II, or a pharmaceutically acceptable salt thereof, is administered to a patient, preferably a mammal, more preferably a human, as a preventative measure against a disease associated with premature translation termination and/or nonsense-mediated mRNA decay.

In a preferred embodiment, it is first determined that the patient is suffering from a disease associate with premature translation termination and/or nonsense-mediated mRNA decay. In another embodiment, the patient has undergone a screening process to determine the presence of a nonsense mutation comprising the steps of screening a subject, or cells extracted therefrom, by an acceptable nonsense mutation screening assay. In a preferred embodiment, the DNA of the patient can be sequenced or subject to Southern Blot, polymerase chain reaction (PCR), use of the Short Tandem Repeat (STR), or polymorphic length restriction fragments (RFLP) analysis to determine if a nonsense mutation is present in the DNA of the patient. Alternatively, it can be determined if altered levels of the protein with the nonsense mutation are expressed in the patient by western blot or other immunoassays. In another embodiment, the patient is an unborn child who has undergone screening in utero for the presence of a nonsense mutation. Administration of a compound of formula I or II can occur either before or after birth. In a related embodiment, the therapy is personalized in that the patient is screened for a nonsense mutation screening assay and treated by the administration of one or more compounds of the invention; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination and/or nonsense-mediated mRNA decay with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell).

Specific methods of the invention further comprise the administration of an additional therapeutic agent (i.e. a therapeutic agent other than a compound of the invention). In certain embodiments of the present invention, the compounds of the invention can be used in combination with at least one other therapeutic agent. Therapeutic agents include, but are not limited to non-opioid analgesics; non-steroid anti-inflammatory agents; antiemetics; β-adrenergic blockers; anticonvulsants; antidepressants; $Ca^{2+}$-channel blockers; anticancer agent and mixtures thereof.

In certain embodiments, the compounds of formula I or II can be administered or formulated in combination with anticancer agents. Suitable anticancer agents include, but are not limited to, alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan and taxol.

In certain embodiments, the compounds of formula I or II can be administered or formulated in combination with antibiotics. In certain embodiments, the antibiotic is a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)). In a preferred embodiment, the antibiotic is active against *Pseudomonas aeruginosa.*

The compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent.

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 0.1 mg to about 2000 mg per day, given as a single once-a-day dose, preferably as divided doses throughout a day. In one embodiment, the daily dose is administered in a single dose or in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompass the above described dosage amounts and dose frequency schedules. Different therapeutically effective amounts may be applicable for different diseases and conditions, as will be readily known by those of ordinary skill in the art. Similarly, amounts sufficient to treat or prevent such diseases, but insufficient to cause, or sufficient to reduce, adverse effects associated with conventional therapies are also encompassed by the above described dosage amounts and dose frequency schedules.

4.5 Pharmaceutical Compositions

Pharmaceutical compositions and single unit dosage forms comprising a compound of the invention, or a pharmaceutically acceptable polymorph, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Pharmaceutical compositions and dosage forms of the invention comprise a compound of the invention, or a pharmaceutically acceptable prodrug, polymorph, salt, solvate, hydrate, or clathrate thereof. Pharmaceutical compositions and dosage forms of the invention typically also comprise one or more pharmaceutically acceptable excipients.

A particular pharmaceutical composition encompassed by this embodiment comprises a compound of the invention, or a pharmaceutically acceptable polymorph, prodrug, salt, solvate, hydrate, or clathrate thereof, and at least one additional therapeutic agent. Examples of additional therapeutic agents include, but are not limited to: anti-cancer drugs and anti-inflammation therapies including, but not limited to, those listed above in Section 4.3.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder.

These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of the invention, or a pharmaceutically acceptable salt, solvate, clathrate, hydrate, polymoprh or prodrug thereof lie within the range of from about 0.1 mg to about 2000 mg per day, given as a single once-a-day dose in the morning but preferably as divided doses throughout the day taken with food. More specifically, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 2000 mg per day as either a single dose or divided doses, depending on the patient's global response.

4.5.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Because of their ease of administration, tablets and capsules represent an advantageous oral dosage unit form, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.5.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.5.4 Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.5.5 Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of formula I or II can also be administered directly to the lung by inhalation (see e.g., Tong et al., PCT Application, WO 97/39745; Clark et al, PCT Application, WO 99/47196, which are herein incorporated by reference). For administration by inhalation, a compound of formula I or II can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound of formula I directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a compound of formula I to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of formula I or II to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver a compound of formula I or II to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics. Inhaled compound of formula I, delivered by nebulizer devices, is currently under investigation as a treatment for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In a particularly preferred embodiment, an electrohydrodynamic ("EHD") aerosol device is used to deliver a compound of formula I or II to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the compound of formula I formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of a compound of formula I or II will be known to the skilled artisan and are within the scope of the invention.

Liquid drug formulations suitable for use with nebulizers and liquid spray devices and EHD aerosol devices will typically include a compound of formula I with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of a compound of formula I or II. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference) A compound of formula I can also be formulated in rectal or vaginal compositions such as suppositories or retention enemas, e.g., containing conventional suppository bases such as cocoa butter or other glycerides.

In addition to the formulations described previously, a compound of formula I or II can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver a compound of formula I or II. Certain organic solvents such as dimethylsulfoxide can also be employed, although usually at the cost of greater toxicity. A compound of formula I can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989, 25, 351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g. Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., *Remington's Pharmaceutical Sciences*, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5. EXAMPLES

The following examples employ methodology which can be used to prepare all of the compounds embodied in this invention, provided the appropriate reagents and substrates are utilized, and minor variations of the described conditions are maintained. Such variations would be easily performed by one of skill in the art without undue experimentation given the description below.

5.1 Example 1

Preparation of 3-[5-(4-Fluoro-phenyl)-[1,2,4]oxadiazol-3-yl]-benzoic acid

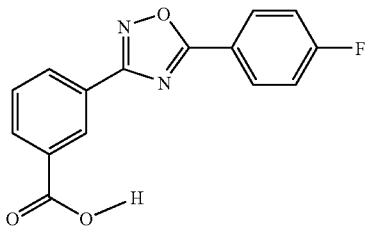

40 g of 2-chlorotrityl chloride resin (Rapp polymere, Germany), was suspended in dry dimethylformamide (200 mL) for 10 min and the solvent was drained. To the resin was added a solution of 3-cyanobenzoic acid (12.71 g, 96.4 mmol) in 300 mL of dimethylformamide and agitated 4 h at room temperature. The solvents were drained and the resin was washed with dichloromethane (3×200 mL×1 min), dimethylformamide (3×200 mL×1 min), methanol (3×200 mL×1 min), and dichloromethane (3×200 mL×1 min). The resin was vacuum dried for 4 h. The desired product was analyzed by cleavage of a small amount of the reacted resin with triethylsilane/trifluoroacetic acid/dichloromethane(10/50/40). LC/MS (ESI) m/z 148 [M+H]$^+$ and 97% purity.

The 3-cyanobenzoic trityl resin in ethanol (300 mL) was agitated for 10 min at room temperature, and then the solvent was drained. To a solution of hydroxy amine hydrochloride (35.81 g, 516 mmol) in ethanol (200 mL) was added diisopropylethylamine (89.3 mL, 516 mmol) and stirred 5 min at room temperature. To the resin was added the reaction mixture and agitated 24 h at 40° C. The solvents were drained, and the resin was washed with dichloromethane (3×200 mL×10 min), dimethylformamide (3×200 mL×10 min), methanol (3×200 mL×10 min), and dichloromethane (3×200 mL×10 min). The resin was vacuum dried for 4 h. The desired product was analyzed by cleavage of a small amount of the reacted resin with triethylsilane/trifluoroacetic acid/dichloromethane (10/50/40). LC/MS (ESI) m/z 181 [M+H]$^+$ and 90% purity.

To a suspension of hydoxyamidine resin (500 mg, 0.4 mmol) in anhydrous dichloromethane (3 mL) was added 4-Fluorobenzoyl chloride (95 uL, 0.8 mmol) and diisopropylethylamine (138 uL, 0.8 mmol). The reaction mixture was agitated overnight at room temperature. The solvents were drained, and the resin was washed with dichloromethane (3×10 mL×10 min), dimethylformamide (3×10 mL×10 min), methanol (3×10 mL×10 min), and dichloromethane (3×10 mL×10 min). The resin was vacuum dried for 4 h. The desired product was analyzed by cleavage of a small amount of the reacted resin with triethylsilane/trifluoroacetic acid/dichloromethane(10/50/40). LC/MS (ESI) m/z 303 [M+H]$^+$ and 65% purity.

To a suspension of acylated resin in anhydrous dichloromethane (1.5 mL) was added 50% trifluoroacetic acid in dichloromethane (1.5 mL). The reaction mixture was agitated 2 h at room temperature. The resin was removed and the filtrate was concentrated under reduced pressure. The residue was dissolved in 10% dimethylformaide in toluene (4 mL) and then stirred for 2 h at 130° C. The solvents were removed and the desired product was purified by preparative LC/MS. LC/MS (ESI) m/z 285 [M+H]$^+$ and 98% purity.

The following compounds are prepared using the procedures described above. Compounds are analyzed by a LC/MS using Electrospray ionization (ESI).

TABLE 2

| Compound | Compound Name | [M + H]$^+$ |
|---|---|---|
| | 3-[5-(3-Chloro-phenyl)-[1,2,4]oxadiazol-3-yl]-benzoic acid | 301.7 |
| | 3-[5-(4-Pentyloxy-phenyl)-[1,2,4]oxadiazol-3-yl]-benzoic acid | 353.4 |
| | 3-(5-Naphthalen-1-yl-[1,2,4]oxadiazol-3-yl)-benzoic acid | 317.3 |
| | 3-(5-p-Tolyl-[1,2,4]oxadiazol-3-yl)-benzoic acid | 281.3 |
| | 3-(5-Biphenyl-4-yl-[1,2,4]oxadiazol-3-yl)-benzoic acid | 343.3 |

TABLE 2-continued

| Compound | Compound Name | [M + H]+ |
|---|---|---|
| | 3-[5-(4-Isobutyl-phenyl)-[1,2,4]oxadiazol-3-yl]-benzoic acid | 323.4 |
| | 3-(5-Phenyl-[1,2,4]oxadiazol-3-yl)-benzoic acid | 267.3 |
| | 3-(5-Cyclohexyl-[1,2,4]oxadiazol-3-yl)-benzoic acid | 273.3 |
| | 3-[5-(3,4,5-Trimethoxy-phenyl)-[1,2,4]oxadiazol-3-yl]-benzoic acid | 357.3 |
| | 3-[5-(4-Nitro-phenyl)-[1,2,4]oxadiazol-3-yl]-benzoic acid | 312.2 |
| | 3-[5-(4-Methoxy-phenyl)-[1,2,4]oxadiazol-3-yl]-benzoic acid | 297.3 |

TABLE 2-continued

| Compound | Compound Name | [M + H]+ |
|---|---|---|
| | 3-[5-(o-tolyl)-[1,2,4]oxadiazol-3-yl]-benzoic acid | 281.3 |
| | 3-(5-Benzo[1,3]dioxol-5-yl-[1,2,4]oxadiazol-33-yl)-benzoic acid | 311.3 |
| | 3-(5-Isopropyl-[1,2,4]oxadiazol-3-yl)-benzoic acid | 233.2 |
| | 3-[5-(3,5-Bis-trifluoromethyl-phenyl)-[1,2,4]oxadiazol-3-yl]-benzoic acid | 403.2 |
| | 3-[5-(4-Trifluoromethyl-phenyl)-[1,2,4]oxadiazol-3-yl]-benzoic acid | 335.2 |
| | 3-[5-(4-Dimethylamino-phenyl)-[1,2,4]oxadiazol-3-yl]-benzoic acid | 310.3 |

TABLE 2-continued

| Compound | Compound Name | [M + H]+ |
|---|---|---|
| | 3-[5-(2-Methoxy-phenyl)-[1,2,4]oxadiazol-3-yl]-benzoic acid | 297.3 |
| | 3-[5-(3-Methoxy-phenyl)-[1,2,4]oxadiazol-3-yl]-benzoic acid | 297.3 |
| | 3-(5-Furan-2-yl-[1,2,4]oxadiazol-3-yl)-benzoic acid | 257.2 |
| | 3-(5-tert-Butyl-[1,2,4]oxadiazol-3-yl)-benzoic acid | 247.3 |
| | 3-(5-Benzo[1,2,5]oxadiazol-5-yl-[1,2,4]oxadiazol-3-yl)-benzoic acid | 309.2 |
| | 3-[5-(4-Chloromethyl-phenyl)-[1,2,4]oxadiazol-3-yl]-benzoic acid | 315.7 |

TABLE 2-continued

| Compound | Compound Name | [M + H]+ |
|---|---|---|
| | 3-[5-(4-tert-Butyl-phenyl)-[1,2,4]oxadiazol-3-yl]-benzoic acid | 323.4 |
| | 3-(5-Butyl-[1,2,4]oxadiazol-3-yl)-benzoic acid | 247.3 |
| | 3-(5-Cyclopropyl-[1,2,4]oxadiazol-3-yl)-benzoic acid | 231.2 |
| | 3-(5-Thiophen-2-yl-[1,2,4]oxadiazol-3-yl)-benzoic acid | 273.3 |
| | 3-(5-Propenyl-[1,2,4]oxadiazol-3-yl)-benzoic acid | 231.2 |
| | 3-(5-Cyanopentyl-[1,2,4]oxadiazol-3-yl)-benzoic acid | 259.3 |

TABLE 2-continued

| Compound | Compound Name | [M + H]+ |
|---|---|---|
| | 3-(5-Thiophen-2-ylmethyl-[1,2,4]oxadiazol-3-yl)-benzoic acid | 287.3 |
| | 3-[5-(4-Chloro-benzyl)-[1,2,4]oxadiazol-3-yl]-benzoic acid | 315.7 |
| | 3-[5-(4-Chloro-phenoxymethyl)-[1,2,4]oxadiazol-3-yl]-benzoic acid | 331.7 |
| | 3-[5-(2-Trifluoromethyl-phenyl)-[1,2,4]oxadiazol-3-yl]-benzoic acid | 335.3 |
| | 3-[5-(2,6-Difluoro-phenyl)-[1,2,4]oxadiazol-3-yl]-benzoic acid | 303.2 |

TABLE 2-continued

| Compound | Compound Name | [M + H]⁺ |
|---|---|---|
| | 3-[5-(4-Ethyl-phenyl)-[1,2,4]oxadiazol-3-yl]-benzoic acid | 296.3 |
| | 3-[5-(3,4-Difluoro-phenyl)-[1,2,4]oxadiazol-3-yl]-benzoic acid | 304.2 |
| | 3-(5-m-Tolyl-[1,2,4]oxadiazol-3-yl)-benzoic acid | 281.3 |
| | 3-[5-(4-Pyrrol-1-yl-phenyl)-[1,2,4]oxadiazol-3-yl]-benzoic acid | 332.0 |
| | 3-(5-Benzyl-[1,2,4]oxadiazol-3-yl)-benzoic acid | 281.3 |
| | 3-(5-Methoxymethyl-[1,2,4]oxadiazol-3-yl)-benzoic acid | 235.2 |

TABLE 2-continued

| Compound | Compound Name | [M + H]+ |
|---|---|---|
| | 3-[5-(2,5-Difluoro-phenyl)-[1,2,4]oxadiazol-3-yl]-benzoic acid | 303.2 |
| | 3-[5-(1-Phenyl-propyl)-[1,2,4]oxadiazol-3-yl]-benzoic acid | 309.3 |
| | 3-[5-(2-Chloro-phhenyl)-[1,2,4]oxadiazol-3-yl]-benzoic acid | 301.7 |
| | 3-[5-(3-Trifluoromethoxy-phenyl)-[1,2,4]oxadiazol-3-yl]-benzoic acid | 351.2 |
| | 3-[5-(4-Fluoro-benzyl)-[1,2,4]oxadiazol-3-yl]-benzoic acid | 299.3 |

TABLE 2-continued

| Compound | Compound Name | [M + H]⁺ |
|---|---|---|
| | 3-[5-(2,5-Dimethyl-furan-3-yl)-[1,2,4]oxadiazol-3-yl]-benzoic acid | 285.3 |
| | 3-[5-(3-Methyl-thiophen-2-yl)-[1,2,4]oxadiazol-3-yl]-benzoic acid | 287.3 |
| | 3-[5-(3-Chloro-phenoxymethyl)-[1,2,4]oxadiazol-3-yl]-benzoic acid | 331.7 |
| | 3-(5-Isoxazol-5-yl-[1,2,4]oxadiazol-3-yl)-benzoic acid | 258.2 |
| | 3-[5-(6-Chloro-pyridin-3-yl)-[1,2,4]oxadiazol-3-yl]-benzoic acid | 302.7 |

TABLE 2-continued

| Compound | Compound Name | [M + H]+ |
|---|---|---|
| | 3-{5-[3-(2-Chloro-phenyl)-5-methyl-isoxazol-4-yl]-[1,2,4]oxadiazol-3-yl}-benzoic acid | 382.8 |
| | 3-{5-[3-(2-Chloro-6-fluoro-phenyl)-5-methyl-isoxazol-4-yl]-[1,2,4]oxadiazol-3-yl}-benzoic acid | 400.0 |
| | 3-(5-Cyclopentylmethyl-[1,2,4]oxadiazol-3-yl)-benzoic acid | 273.3 |
| | 3-[5-(2,4-Difluoro-phenyl)-[1,2,4]oxadiazol-3-yl]-benzoic acid | 303.2 |
| | 3-(5-Pyridin-3-yl-[1,2,4]oxadiazol-4-yl)-benzoic acid | 268.2 |

TABLE 2-continued

| Compound | Compound Name | [M + H]+ |
|---|---|---|
| | 3-(5-Pyridin-4-yl-[1,2,4]oxadiazol-3-yl)-benzoic acid | 268.2 |
| | 3-(5-Cyclobutyl-[1,2,4]oxadiazol-3-yl)-benzoic acid | 245.2 |
| | 3-[5-(4-Methoxy-benzyl)-[1,2,4]oxaidazol-3-yl]-benzoic acid | 311.3 |
| | 3-[5-(3,4-Dimethoxy-phenyl)-[1,2,4]oxadiazol-3-yl]-benzoic acid | 327.3 |
| | 3-[5-(2-Chloro-pyridin-3-yl)-[1,2,4]oxadiazol-3-yl]-benzoic acid | 302.7 |

TABLE 2-continued

| Compound | Compound Name | [M + H]⁺ |
|---|---|---|
| | 3-[5-(1-Acetyl-piperidin-4-yl)-[1,2,4]oxadiazol-3-yl]-benzoic acid | 316.3 |
| | 3-(5-Benzo[b]thiophen-2-yl-[1,2,4]oxadiazol-3-yl)-benzoic acid | 323.3 |
| | 3-[5-(3-Dimethylamino-phenyl)-[1,2,4]oxadiazol-3-yl]-benzoic acid | 310.3 |
| | 3-[5-(2,3-Difluoro-phenyl)-[1,2,4]oxadiazol-3-yl]-benzoic acid | 303.2 |
| | 3-[5-(2-Fluoro-5-methyl-phenyl)-[1,2,4]oxadiazol-3-yl]-benzoic acid | 299.3 |

TABLE 2-continued

| Compound | Compound Name | [M + H]+ |
|---|---|---|
| | 3-[5-(2-Methylsulfanyl-pyridin-3-yl)-[1,2,4]oxadiazol-3-yl]-benzoic acid | 314.3 |
| | 3-[5-(2,2-Difluoro-benzo[1,3]dioxol-5-yl)-[1,2,4]oxadiazol-3-yl]-benzoic acid | 347.2 |
| | 2-Fluoro-5-[5-(4-fluorro-phenyl)-[1,2,4]oxadiazol-3-yl]-benzoic acid | 303.2 |
| | 3-[5-(4-Bromo-2-fluoro-phenyl)-[1,2,4]oxadiazol-3-yl]-benzoic acid | 364.1 |
| | 3-[5-(3-Fluoro-biphenyl-4-yl)-[1,2,4]oxadiazol-3-yl]-benzoic acid | 361.3 |
| | 3-[5-(3-Fluoro-phenyl)-[1,2,4]oxadiazol-3-yl]-benzoic acid | 285.2 |

TABLE 2-continued

| Compound | Compound Name | [M + H]+ |
|---|---|---|
| | 3-[5-(2,3-Difluoro-phenyl)-[1,2,4]oxadiazol-3-yl]-benzoic acid | 303.2 |
| | 3-[5-(2-Fluoro-5-methyl-phenyl)-[1,2,4]oxadiazol-3-yl]-benzoic acid | 299.3 |
| | 3-[5-(2-Methylsulfanyl-pyridin-3-yl)-[1,2,4]oxadiazol-3-yl]-benzoic acid | 314.3 |
| | 3-[5-(2,2-Difluoro-benzo[1,3]dioxol-5-yl)-[1,2,4]oxadiazol-3-yl]-benzoic acid | 347.2 |
| | 3-[5-(2-Fluoro-phenyl)-[1,2,4]oxadiazol-3-yl]-benzoic acid | 285.1 |

TABLE 2-continued

| Compound | Compound Name | [M + H]+ |
|---|---|---|
| | 3-[5-(4-Fluoro-phenyl)-[1,2,4]oxadiazol-3-yl]-benzoic acid | 285.2 |
| | 3-[5-(4-Cyano-phenyl)-[1,2,4]oxadiazol-3-yl]-benzoic acid | 292.08 |
| | 3-[5-(2-Fluoro-phenyl)-[1,2,4]oxadiazol-3-yl]-benzoic acid sodium salt | 306.04 |
| | 3-[5-(2-Fluoro-phenyl)-[1,2,4]oxadiazol-3-yl]-benzoic acid methyl ester | 299.08 |

5.2 Example 2

Preparation of 3-[5-(2-Fluoro-phenyl)-[1,2,4]oxadiazol-3-yl]-benzoic acid

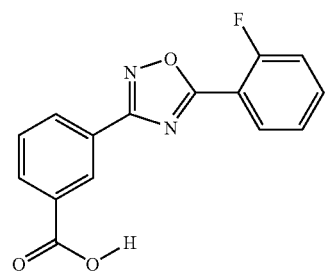

To a solution of 3-Cyanobenzoic acid (44.14 g, 300 mmol) in DMF (0.6 L) was added $K_2CO_3$ (62.19 g, 450 mmol) and then stirred for 30 min at room temperature. To the suspension was added methyl iodide (28 mL, 450 mmol) over 20 min, and the reaction mixture was stirred further 4 h at room temperature. The reaction mixture was poured to 1.2 L of ice water and stirred for 30 min, and the precipitate was filtered off. The white cake was dissolved in methanol (70 mL), and then re-precipitated in cold water. The desired product was obtained as a white powder with 79% yield (38 g, 99% purity by LC/UV). $^1$H-NMR (CDCl$_3$) δ 8.85 (2H), 8.28 (1H), 8.02 (1H), 4.17 (3H).

To a solution of 3-Cyanobenzoic acid methyl ester (50 g, 310 mmol) in ethanol (500 mL) was added 50% aqueous hydroxylamine (41 mL, 620 mmol) at room temperature. The reaction mixture was stirred for 1 h at 100° C. and the solvents were removed under reduced pressure. The oily residue was dissolved in 20/80 ethanol/toluene (50 mL×2) and then concentrated again. The desired ester (61 g, quan. yield) was obtained as a white powder with 98% purity (LC/UV). $^1$H-NMR (CDCl$_3$) δ 9.76 (1H), 8.24 (1H), 7.82 (2H), 7.51 (1H), 5.92 (2H), 3.82 (3H).

To a solution of 3-(N-Hydroxycarbamimidoyl)-benzoic acid methyl ester (60 g, 310 mmol) in anhydrous THF (200 mL) was added diisopropylethylamine (75 mL, 434 mmol) at 5° C., and then to the mixture was added 2-fluorobenzoyl chloride (48.1 mL, 403 mmol) over 20 min. The reaction mixture was stirred for 1 h at room temperature. The precipitate was filtered off and the filtrate was concentrated under reduced pressure. The residue was dissolved in ethylacetate (400 mL) and then washed with water (200 mL×2). The solvent was removed under reduced pressure and the desired product was crystallized in 60% ethylacetate in hexane to yield the desired product (81 g, 83% yield) as a white solid. $^{1}$H-NMR (CDCl$_{3}$) δ 8.18 (1H), 8.03 (2H), 7.48 (2H), 7.18 (2H), 5.61 (2H), 3.82 (3H).

44 g of 3-(N-2-Fluorobenzoylcarbamimidoyl)-benzoic acid methyl ester in toluene (500 mL) was refluxed for 4 h at 130° C. using Dean-Stark apparatus. The reaction mixture was stirred at 5° C. for 18 h. The white precipitate was filtered off and the filtrate was concentrated, crystallized again in toluene. The desired oxadiazole (38 g, 92% yield) was obtained as a white solid with 99% purity (LC/UV). $^{1}$H-NMR (CDCl$_{3}$) δ 8.91 (1H), 8.38 (1H), 8.15 (2H), 7.62 (2H), 7.35 (2H), 3.95 (3H)

To a solution of 3-[5-(2-Fluoro-phenyl)-[1,2,4]oxadiazol-3-yl]-benzoic acid methyl ester (33 g, 111 mol) in THF (400 mL) was added 1.5M aqueous NaOH (100 mL, 144 mmol). The reaction mixture was refluxed for 2h at 100° C. The organic solvent was removed under reduced pressure and the aqueous solution was stirred 2 h at 5° C. The white precipitate was filtered off and the filtrate was concentrated and precipitated again in water. The white cake was washed with cold water and then dried using lyophilizer. The desired salt (33 g, 96% yield) was obtained as a white powder with 98.6% purity (LC/UV).

To a solution of 3-[5-(2-Fluoro-phenyl)-[1,2,4]oxadiazol-3-yl]-benzoic acid methyl ester (3.3 g, 11 mmol) in THF (40 mL) was added 1.5M aqueous NaOH (10 mL, 14 mmol). The reaction mixture was refluxed for 2 h at 100° C. The organic solvent was removed and the aqueous solution was diluted with water (50 mL), and then acidified with aqueous HCl. The white precipitate was filtered off and the white cake was washed with cold water and then dried using lyophilizer. The desired acid (3.0 g, 96% yield) was obtained as a white powder with 98% purity (LC/UV). Melting point 242° C.; IR υ 3000 (Aromatic C—H), 1710 (C=O); $^{1}$H-NMR (D$_{6}$-DMSO) δ 8.31 (1H), 8.18 (2H), 8.08 (1H), 7.88 (2H), 7.51 (2H); $^{13}$C-NMR (D$_{6}$-DMSO) δ 172.71, 167.38, 166.48, 161.25, 135.80, 132.24, 131.79, 131.79, 131.08, 130.91, 129.81, 127.76, 125.48, 117.38, 111.70; $^{19}$F-NMR (D$_{6}$-DMSO) δ 109.7.

The following compounds are prepared using the procedures described above.

TABLE 3

| Compound | Compound Name | [M + H]$^{+}$ |
| --- | --- | --- |
|  | 3-[5-(4-Fluoro-phenyl)-[1,2,4]oxadiazol-3-yl]-benzoic acid | 285.2 |
|  | 3-[5-(2-Fluoro-phenyl)-[1,2,4]oxadiazol-3-yl]-benzoic acid | 285.1 |
|  | 3-[5-(3-Fluoro-phenyl)-[1,2,4]oxadiazol-3-yl]-benzoic acid | 285.2 |

TABLE 3-continued

| Compound | Compound Name | [M + H]+ |
|---|---|---|
|  | 4-Fluoro-3-[5-(4-fluoro-phenyl)-[1,2,4]oxadiazol-3-yl]-benzoic acid | 303.2 |
|  | 5-[5-(4-Fluoro-phenyl)-[1,2,4]oxadiazol-3-yl]-2-methoxy-benzoic acid | 315.3 |
|  | 3-[5-(4-Chloro-2-fluoro-phenyl)-[1,2,4]oxadiazol-3-yl]-benzoic acid | 319.7 |
|  | 3-[5-(3-Fluoro-biphenyl-4-yl)-[1,2,4]oxadiazol-3-yl]-benzoic acid | 361.3 |
|  | 3-[5-(4-Bromo-2-fluoro-phenyl)-[1,2,4]oxadiazol-3-yl]-benzoic acid | 364.1 |
|  | 3-[5-(4-Fluoro-phenyl)-[1,2,4]oxadiazol-3-yl]-benzoic acid methyl ester | 299.08 |
|  | 5-[5-(4-Fluoro-phenyl)-[1,2,4]oxadiazol-3-yl]-2-methoxy-benzoic acid | 339.13 |

TABLE 3-continued
| Compound | Compound Name | [M + H]+ |
|---|---|---|
| 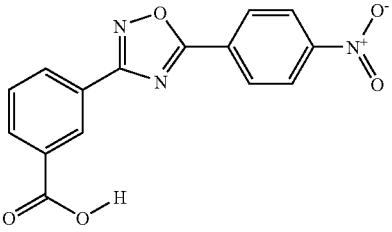 | 3-[5-(4-Bromo-2-fluoro-phenyl)-[1,2,4]oxadiazol-3-yl]-benzoic acid | 365.05 |
| 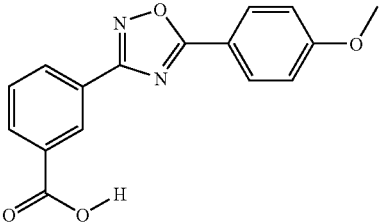 | 3-[5-(3-Fluoro-biphenyl-4-yl)-[1,2,4]oxadiazol-3-yl]-benzoic acid | 361.16 |
| 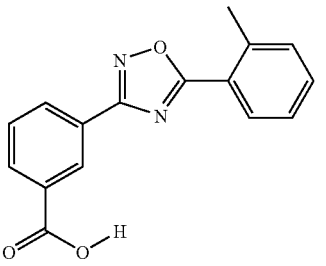 | 3-[5-(6-Pyrrolidin-1-yl-pyridin-3-yl)-[1,2,4]oxadiazol-3-yl]-benzoic acid | 337.20 |
| 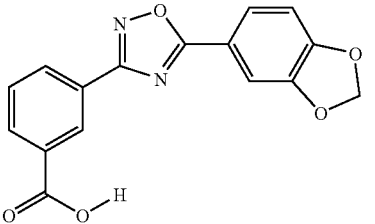 | 3-[5-(6-Morpholin-4-yl-pyridin-3-yl)-[1,2,4]oxadiazol-3-yl]-benzoic acid | 353.18 |
| 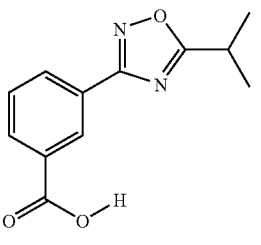 | 3-[5-(3,4,5,6-Tetrahydro-2H-[1,2']bipyridinyl-5'-yl)-[1,2,4]oxadiazol-3-yl]-benzoic acid | 351.18 |
| 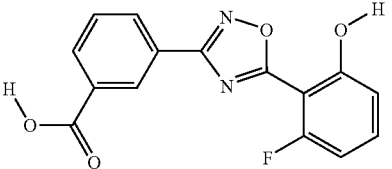 | 3-[5-(2-Fluoro-6-hydroxy-phenyl)-[1,2,4]oxadiazol-3-yl]-benzoic acid | 301.18 |

TABLE 3-continued

| Compound | Compound Name | [M + H]⁺ |
|---|---|---|
| | 3-[5-(2-Fluoro-phenyl)-[1,2,4]oxadiazol-3-yl]-benzoic acid 2-methoxy-ethyl ester | 343.16 |
| | 3-[5-(2-Fluoro-phenyl)-[1,2,4]oxadiazol-3-yl]-benzoic acid 2-(2-methoxy-ethoxy)-ethyl ester | 387.49 |
| | 3-[5-(2-Fluoro-phenyl)-[1,2,4]oxadiazol-3-yl]-benzoic acid 2-[2-(2-methoxy-ethoxy)-ethoxy]-ethyl ester | 431.31 |
| | 3-[5-(2-Fluoro-phenyl)-[1,2,4]oxadiazol-3-yl]-benzoic acid 2-{2-[2-(2-methoxy-ethoxy)-ethoxy]-ethoxy} ethyl ester | 475.26 |
| | 3-[5-(2-Fluoro-phenyl)-[1,2,4]oxadiazol-3-yl]-benzoic acid 2-(2-{2-[2-(2-methoxy-ethoxy)-ethoxy]-ethoxy}-ethoxy)-ethyl ester | 519.33 |
| | 3-[5-(2-Fluoro-phenyl)-[1,2,4]oxadiazol-3-yl]-benzoic acid 2-[2-(2-{2-[2-(2-hydroxy-ethoxy)-ethoxy]-ethoxy}-ethoxy)-ethoxy]-ethyl ester | 549.35 |

TABLE 3-continued

| Compound | Compound Name | [M + H]⁺ |
|---|---|---|
| | 3-[5-(4-Amino-phenyl)-[1,2,4]oxadiazol-3-yl]-benzoic acid | 282.20 |
| | 3-[5-(4-Azido-phenyl)-[1,2,4]oxadiazol-3-yl]-benzoic acid | 309.20 |
| | 3-[5-(4-Benzyloxy-phenyl)-[1,2,4]oxadiazol-3-yl]-benzoic acid | 373.16 |

5.3 Example 3

Identification and Characterization of Compounds that Promote Nonsense Suppression and/or Modulate Translation Termination The assays described above in Section 4.2 were used in two high throughput screens. Compounds were screened in the cell-based and biochemical assays. Compounds were tested, resynthesized and tested again to confirm chemical structures. 3-[2-(4-Isopropyl-3-methyl-phenoxy)-acetylamino]-benzoic acid, sodium salt was characterized further with the in vitro luciferase nonsense suppression assay. To ensure that the observed nonsense suppression activity of the selected compounds was not limited to the rabbit reticulocyte assay system, HeLa cell extract was prepared and optimized (Lie & Macdonald, 1999, *Development* 126(22):4989-4996 and Lie & Macdonald, 2000, *Biochem. Biophys. Res. Commun.* 270 (2):473-481).

5.4 Example 4

Characterization of Compounds that Increase Nonsense Suppression and Produce Functional Protein It was previously demonstrated that compounds of the invention increase the level of nonsense suppression in the biochemical assay three to four fold over untreated extracts. To determine whether compounds also function in vivo, a stable cell line harboring the UGA nonsense-containing luciferase gene was treated with selected compounds. Cells were grown in standard medium supplemented with 1% penicillin-streptomycin (P/S) and 10% fetal bovine serum (FBS) to 70% confluency and split 1:1 the day before treatment. On the following day, cells were trypsinized and 40,000 cells were added to each well of a 96-well tissue culture dish. Serial dilutions of each compound were prepared to generate a six-point dose response curve spanning 2 logs (30 µM to 0.3 µM). The final concentration of the DMSO solvent remained constant at 1% in each well. Cells treated with 1% DMSO served as the background standard, and cells treated with gentamicin served as a positive control.

5.5 Example 5

3-[2-(4-isopropyl-3-methyl-phenoxy)-acetylamino]-benzoic acid, sodium salt Alters the Accessibility of the Chemical Modifying Agents to Specific Nucleotides in the 28 S rRNA Previous studies have demonstrated that gentamicin and other members of the aminoglycoside family that decrease the fidelity of translation bind to the A site of the 16S rRNA. By chemical footprinting, UV cross-linking and NMR, gentamicin has been shown to bind at the A site (comprised of nucleotides 1400-1410 and 1490-1500, *E. coli* numbering) of the rRNA at nucleotides 1406, 1407, 1494, and 1496 (Moazed & Noller, 1987, *Nature* 327(6121):389-394; Woodcock et al., 1991, *EMBO J.* 10(10):3099-3103; and Schroeder et al., 2000, *EMBO J.* 19:1-9

Ribosomes prepared from HeLa cells were incubated with the small molecules (at a concentration of 100 µM), followed by treatment with chemical modifying agents (dimethyl sulfate [DMS] and kethoxal [KE]). Following chemical modification, rRNA was phenol-chloroform extracted, ethanol precipitated, analyzed in primer extension reactions using end-labeled oligonucleotides hybridizing to different regions of the three rRNAs and resolved on 6% polyacrylamide gels. The probes used for primer extension cover the entire 18S (7 oligonucleotide primers), 28S (24 oligonucleotide primers), and 5S (one primer) rRNAs. Controls in these experiments include DMSO (a control for changes in rRNA accessibility induced by DMSO), paromomycin (a marker for 18S rRNA binding), and anisomycin (a marker for 28S rRNA binding).

The results of these foot-printing experiments indicated that 3-[2-(4-Isopropyl-3-methyl-phenoxy)-acetylamino]-benzoic acid, sodium salt alters the accessibility of the chemical modifying agents to specific nucleotides in the 28S rRNA. More specifically, the regions protected by 3-[2-(4-Isopropyl-3-methyl-phenoxy)-acetylamino]-benzoic acid, sodium salt include: (1) a conserved region in the vicinity of the peptidyl transferase center (domain V) implicated in peptide bond formation and (2) a conserved region in domain II that may interact with the peptidyl transferase center based on binding of vemrnamycinin B to both these areas.

5.6 Example 6

Readthrough of Premature Termination Codons in Cell-based Disease Models

To address the effects of the nonsense-suppressing compounds on mRNAs altered in specific inherited diseases, a bronchial epithelial cell line harboring a nonsense codon at amino acid 1282 (W1282X) was treated with 3-[2-(4-Isopropyl-3-methyl-phenoxy)-acetylamino]-benzoic acid, sodium salt (20 μM) and CFTR function was monitored as a cAMP-activated chloride channel using the SPQ assay (Yang et al., 1993, Hum Mol Genet. 2(8):1253-1261 and Howard et al., 1996, Nat Med. 2(4):467-469). These experiments showed that cAMP treatment of these cells resulted in an increase in SPQ fluorescence, consistent with stimulation of CFTR-mediated halide efflux. No increase in fluorescence was observed when cells were not treated with compound or if the cells were not stimulated with cAMP. These results indicate that the full-length CFTR expressed from this nonsense-containing allele following compound treatment also functions as a cAMP-stimulated anion channel, thus demonstrating that cystic fibrosis cell lines increase chloride channel activity when treated with 3-[2-(4-Isopropyl-3-methyl-phenoxy)-acetylamino]-benzoic acid, sodium salt.

5.7 Example 7

Primary Cells from the mdx Nonsense-containing Mouse Express Full-length dystrophin protein when Treated with 3-[2-(4-isopropyl-3-methyl-phenozy)-acetylamino]benzoic acid, sodium salt The mutation in the mdx mouse that premature termination of the 427 kDa dystrophin polypeptide has been shown to be a C to T transition at position 3185 in exon 23 (Sicinski et al., 1989, Science. 244(4912):1578-1580). Mouse primary skeletal muscle cultures derived from 1-day old mdx mice were prepared as described previously (Barton-Davis et al., 1999, *J Clin Invest*. 104(4):375-381). Cells were cultured for 10 days in the presence of 3-[2-(4-Isopropyl-3-methyl-phenoxy)-acetylamino]-benzoic acid, sodium salt (20 μM). Culture medium was replaced every four days and the presence of dystrophin in myoblast cultures was detected by immunostaining as described previously (Barton-Davis et al., 1999, J Clin Invest. 104(4):375-381). A primary monoclonal antibody to the C-terminus of the dystrophin protein (F19A12) was used undiluted and rhodamine conjugated anti-mouse IgG was used as the secondary antibody. The F19A12 antibody will detect the full-length protein produced by suppression of the nonsense codon. Staining was viewed using a Leica DMR microscope, digital camera, and associated imaging software at the University of Pennsylvania.

5.8 Example 8

Readthrough of Premature Termination Codons in the mdx Mouse

As previously described (Barton-Davis et al., 1999, *J Clin Invest*. 104(4):375-381), compound was delivered by Alzet osmotic pumps implanted under the skin of anesthetized mice. Two doses of 3-[2-(4-Isopropyl-3-methyl-phenoxy)-acetylamino]-benzoic acid, sodium salt were administered. Gentamicin served as a positive control and pumps filled with solvent only served as the negative control. Pumps were loaded with appropriate compound such that the calculated doses to which tissue was exposed were 10 μM and 20 μM. The gentamicin concentration was calculated to achieve tissue exposure of approximately 200 μM. In the initial experiment, mice were treated for 14 days, after which animals were anesthetized with ketamine and exsanguinated. The tibialis anterior (TA) muscle of the experimental animals was then excised, frozen, and used for immunofluorescence analysis of dystrophin incorporation into striated muscle. The presence of dystrophin in TA muscles was detected by immunostaining, as described previously (Barton-Davis et al., 1999, *J Clin Invest*. 104(4):375-381).

5.9 Example 9

200 Mg Dosage Capsule

Table 3 illustrates a batch formulation and single dosage formulation for a 200 mg single dose unit, i.e., about 40 percent by weight.

TABLE 3

Formulation for 200 mg capsule

| Material | Percent By Weight | Quantity (mg/tablet) | Quantity (kg/batch) |
|---|---|---|---|
| Compound of the invention | 40.0% | 200 mg | 16.80 kg |
| Pregelatinized Corn Starch, NF5 | 9.5% | 297.5 mg | 24.99 kg |
| Magnesium Stearate | 0.5% | 2.5 mg | 0.21 kg |
| Total | 100.0% | 500 mg | 42.00 kg |

The pregelatinized corn starch (SPRESS B-820) and compound of the invention components are passed through a 710 μm screen and then are loaded into a Diffusion Mixer with a baffle insert and blended for 15 minutes. The magnesium stearate is passed through a 210 μm screen and is added to the Diffusion Mixer. The blend is then encapsulated in a size #0 capsule, 500 mg per capsule (8400 capsule batch size) using a Dosator type capsule filling machine.

5.10 Example 10

100 Mg Oral Dosage Form

Table 4 illustrates a batch formulation and a single dose unit formulation containing 100 mg of a compound of the invention.

TABLE 4

Formulation for 100 mg tablet

| Material | Percent by Weight | Quantity (mg/tablet) | Quantity (kg/batch) |
| --- | --- | --- | --- |
| compound of the invention | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and compound of the invention components are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The compound is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

5.11 Example 11

Aerosal Dosage Form

A concentrate is prepared by combining a compound of the invention, and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers that have a metered valve which is designed to provide 100 inhalations of the composition of the invention.

Each container is provided with the following:

| | |
| --- | --- |
| compound of the invention | 0.0141 g |
| trichloromonofluoromethane | 1.6939 g |
| dichlorodifluoromethane | 3.7028 g |
| dichlorotetrafluoroethane | 1.5766 g |
| total | 7.0000 g |

What is claimed is:

1. A compound, 3-[5-(2-Fluoro-phenyl)-[1,2,4]oxadiazol-3-yl]-benzoic acid, having the structure:

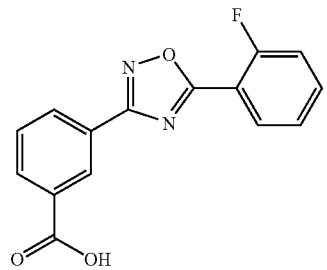

or a pharmaceutically acceptable salt or solvate thereof.

2. A pharmaceutically acceptable hydrate of a compound of claim 1.

3. A pharmaceutical composition comprising 3-[5-(2-Fluoro-phenyl)-[1,2,4]oxadiazol-3-yl]-benzoic acid or a pharmaceutically acceptable salt or solvate thereof and a pharmaceutically acceptable carrier, excipient or diluent.

4. The pharmaceutical composition of claim 3, comprising 0.1 mg to 2000 mg of 3-[5-(2-Fluoro-phenyl)-[1,2,4]oxadiazol-3-yl]-benzoic acid or a pharmaceutically acceptable salt or solvate thereof.

5. The pharmaceutical composition of claim 4, comprising 5 mg to about 500 mg of 3-[5-(2-Fluoro-phenyl)-[1,2,4]oxadiazol-3-yl]-benzoic acid or a pharmaceutically acceptable salt or solvate thereof.

6. The pharmaceutical composition of claim 3 suitable for oral, parenteral, mucosal, transdermal or topical administration.

7. The pharmaceutical composition of claim 6 suitable for oral administration.

8. The pharmaceutical composition of claim 7 in solid form.

9. The pharmaceutical composition of claim 8, wherein the composition is a powder.

10. The pharmaceutical composition of claim 8, wherein the composition is a tablet.

11. The pharmaceutical composition of claim 8, wherein the composition is a capsule.

12. The pharmaceutical composition of claim 7 in liquid form.

13. The pharmaceutical composition of claim 12, wherein the composition is a suspension.

14. The pharmaceutical composition of claim 13, wherein the suspension is aqueous.

15. A single unit dosage form comprising solid 3-[5-(2-Fluoro-phenyl)-[1,2,4]oxadiazol-3-yl]-benzoic acid or a pharmaceutically acceptable salt or solvate thereof and a pharmaceutically acceptable carrier, excipient or diluent.

16. The single unit dosage form of claim 15, comprising 0.1 mg to 2000 mg of 3-[5-(2-Fluoro-phenyl)-[1,2,4]oxadiazol-3-yl]-benzoic acid or a pharmaceutically acceptable salt or solvate thereof.

17. The single unit dosage form of claim 16, comprising 5 mg to about 500 mg of 3-[5-(2-Fluoro-phenyl)-[1,2,4]oxadiazol-3-yl]-benzoic acid or a pharmaceutically acceptable salt or solvate thereof.

18. The single unit dosage form of claim 15 suitable for oral, parenteral, mucosal, transdermal or topical administration.

19. The single unit dosage form of claim 18 suitable for oral administration.

20. The single unit dosage form of claim 15, wherein the dosage form is a powder.

21. The single unit dosage form of claim 15, wherein the dosage form is a tablet.

22. The single unit dosage form of claim 15, wherein the dosage form is a capsule.

23. The composition of claim 3, wherein the composition is sterile.

24. The single unit dosage form of claim 15, wherein the single unit dosage form is sterile.

* * * * *